United States Patent
Zhou et al.

(10) Patent No.: US 12,351,795 B2
(45) Date of Patent: Jul. 8, 2025

(54) **RECOMBINANT *ESCHERICHIA COLI* FOR PRODUCING L-TYROSINE AND APPLICATION THEREOF**

(71) Applicant: Jiangnan University, Wuxi (CN)

(72) Inventors: Jingwen Zhou, Wuxi (CN); Jian Chen, Wuxi (CN); Jurong Ping, Wuxi (CN); Weizhu Zeng, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 18/428,104

(22) Filed: Jan. 31, 2024

(65) Prior Publication Data

US 2024/0166986 A1 May 23, 2024

(30) Foreign Application Priority Data

Feb. 21, 2023 (CN) .......................... 202310143869.0

(51) Int. Cl.
| | |
|---|---|
| *C12N 1/20* | (2006.01) |
| *C12N 9/10* | (2006.01) |
| *C12N 9/12* | (2006.01) |
| *C12N 15/70* | (2006.01) |
| *C12P 13/22* | (2006.01) |
| *C12R 1/19* | (2006.01) |

(52) U.S. Cl.
CPC .............. *C12N 1/20* (2013.01); *C12N 9/1022* (2013.01); *C12N 9/1294* (2013.01); *C12N 15/70* (2013.01); *C12P 13/22* (2013.01); *C12R 2001/19* (2021.05); *C12Y 202/01001* (2013.01); *C12Y 207/09002* (2013.01)

(58) Field of Classification Search
CPC ...... C12N 1/20; C12N 9/1022; C12N 9/1294; C12N 15/70; C12N 9/0006; C12N 9/88; C12N 9/0008; C12N 9/001; C12N 9/1085; C12N 9/90; C12N 2800/101; C12P 13/22; C12P 13/225; C12R 2001/19; C12Y 202/01001; C12Y 207/09002; C12Y 102/03003; C12Y 103/01012; C12Y 205/01054; C12Y 401/02009; C12Y 401/03027; C12Y 402/01051; C12Y 504/99005; Y02A 50/30; C07K 14/245
See application file for complete search history.

(56) References Cited

U.S. PATENT DOCUMENTS

| | | | | |
|---|---|---|---|---|
| 4,743,546 | A | * 5/1988 | Backman | ............... C12N 15/52 435/320.1 |
| 2003/0054503 | A1 | * 3/2003 | Rieping | ............... C07K 14/245 435/106 |
| 2008/0009041 | A1 | * 1/2008 | Mizoguchi | ............. C12P 13/08 435/71.1 |

OTHER PUBLICATIONS

Singh RK et al. Protein Engineering Approaches in the Post-Genomic Era. 2017. Current Protein and Peptide Science. 2017. 18,1-11. (Year: 2017).*
Zhang M et al. Propagated Perturbations from a Peripheral Mutation Show Interactions Supporting WW Domain Thermostability. 2018. Structure. 26.1474-1485. (Year: 2018).*
Anderson, J. Part:BBa_J23119. Registry of Standard Biological Parts. Aug. 24, 2006. https://parts.igem.org/Part:BBa_J23119. Accessed Oct. 18, 2024. (Year: 2006).*
Zhou H, Liao X, Wang T, Du G, Chen J. Enhanced l-phenylalanine biosynthesis by co-expression of pheAfbr and aroFwt. Bioresource Technology. Jun. 2010;101(11):4151-6. (Year: 2010).*
Lütke-Eversloh T, Stephanopoulos G. L-Tyrosine production by deregulated strains of *Escherichia coli*. Appl Microbiol Biotechnol. May 1, 2007;75(1):103-10. (Year: 2007).*

* cited by examiner

*Primary Examiner* — Paul J Holland
*Assistant Examiner* — Adam Christopher Labonte
(74) *Attorney, Agent, or Firm* — IPRO, PLLC; Na Xu

(57) ABSTRACT

Disclosed is recombinant *Escherichia coli* for producing L-tyrosine and application thereof, and belongs to the technical fields of genetic engineering and bioengineering. According to the present disclosure, genes aroP and tyrP are knocked out, expresses the endogenous gene yddG of *E. coli*, then heterologously expresses fpk from *Bifidobacterium adolescentis*, expresses the endogenous genes ppsA and tktA of *E. coli*, and then expresses aroG$^{fbr}$ and tyrA$^{fbr}$. Knocking out tyrR, trpE and pheA, so that the synthesis flux of L-tyrosine is increased. Finally, an endogenous gene poxB is knocked out to realize stable fermentation performance at high glucose concentration.

10 Claims, 2 Drawing Sheets
Specification includes a Sequence Listing.

RECOMBINANT *ESCHERICHIA COLI* FOR PRODUCING L-TYROSINE AND APPLICATION THEREOF

REFERENCE TO SEQUENCE LISTING

The instant application contains a Sequence Listing in XML format as a file named "YGHY-2023-39-SEQ.xml", created on Jan. 16, 2024, of 108 kB in size, and which is hereby incorporated by reference in its entirety.

TECHNICAL FIELD

The present disclosure relates to recombinant *Escherichia Coli* for producing L-tyrosine and application thereof, and belongs to the technical fields of genetic engineering and bioengineering.

BACKGROUND

L-tyrosine (Tyr), as an essential amino acid, is an aromatic amino acid among 20 amino acids forming proteins, which has been widely used in food, feed, medicine and other fields. The L-tyrosine can promote synthesis of catecholamines, thyroid hormones and melanin in human bodies, which has an important effect on development and metabolism of humans and animals. In medicine, the L-tyrosine is used as a main raw material for synthesis of many drugs such as thyroid hormones, epinephrine and levodopa.

At present, traditional production methods for the L-tyrosine include a protein hydrolysis method, a chemical synthesis method, an enzyme method and a microbial fermentation method. According to the protein hydrolysis method, also known as an extraction method, natural protein resources, such as casein, swine blood meal, animal hoofs, horns, hairs and other raw materials are used for separating and extracting the L-tyrosine through hydrolysis, concentration, crystallization, decolorization and other steps. According to an enzyme conversion method, phenol, an ammonia salt and pyruvic acid are used as precursors and converted by tyrosinase. However, the enzyme is easily inactivated, and reaction conditions are strict, so that the enzyme method is not used for industrial preparation of the L-tyrosine in a large scale. According to the chemical synthesis method, racemic DL-tyrosine is synthesized by hydroxylation of L-phenylalanine or by condensation of p-hydroxyamphetamine and hydantoin, alkali hydrolysis, ammonia conversion and other steps, and the L-tyrosine needs to be further separated, resulting in that the process is complicated, and the efficiency is low. According to the microbial fermentation method, biomass raw materials are used to achieve de novo synthesis of tyrosine, so that the production cost is greatly reduced. Compared with the protein hydrolysis method and an enzyme hydrolysis method, the microbial fermentation method has the advantages of short cycle, high conversion rate, simple separation and purification steps and the like. Since the yield of existing tyrosine producing bacteria is low, it is difficult to achieve industrial production in a large scale. It is urgent to construct a recombinant strain capable of producing L-tyrosine efficiently and to establish a microbial fermentation method with higher yield.

SUMMARY

In order to solve the above technical problems, the present disclosure provides recombinant *Escherichia coli* for synthesizing L-tyrosine. *E. coli*, as an original strain, is subjected to at least one of the following improvements:

(1) knocking out endogenous aroP and tyrP to block the transport of L-tyrosine from the outside of cells to the inside of cells of *E. coli*;

(2) overexpressing endogenous yddG to improve the ability of *E. coli* to transport L-tyrosine from the outside of cells to the inside of cells;

(3) expressing phosphoketolase (fpk) from *Bifidobacterium adolescentis* and endogenous genes ppsA and tktA of *E. coli* to effectively guide a carbon metabolism flow of glucose to synthesis of L-tyrosine;

(4) expressing a mutant aroG$^{fbr}$ of aroG from *E. coli*, where the mutant is a mutant relieving feedback inhibition of an aromatic amino acid on 3-deoxy-D-arabino-heptulosonate-7-phosphate synthase;

(5) expressing a mutant tyrA$^{fbr}$ of tyrA from *E. coli*, where the mutant is used for relieving the effect of excessive accumulation of L-tyrosine on chorismate mutase and prephenate dehydrogenase, so that the synthesis flux of L-tyrosine is effectively increased;

(6) knocking out endogenous pheA and trpE to block some branches of a synthetic route of a shikimic acid pathway, so that more metabolism flows are used for synthesizing L-tyrosine;

(7) expressing endogenous genes ppsA and tktA of *E. coli* to increase precursor supply of a shikimic acid pathway and increase the synthesis flux of L-tyrosine; and (8) knocking out a gene poxB to reduce the accumulation of acetic acid in a fermentation process and realize fermentation at high glucose concentration.

The present disclosure provides recombinant *Escherichia coli* for synthesizing L-tyrosine efficiently. The recombinant *E. coli* is obtained by using *E. coli* as an original strain and subjecting the strain to any one of the following gene editing processes (a)-(d):

(a) knocking out a gene pheA encoding and fusing chorismate mutase/prephenate dehydratase, a gene trpE encoding an anthranilate synthetase subunit TrpE, a gene tyrR encoding a DNA binding transcription double regulator TyrR, a gene aroG$^{fbr}$ freely expressing and encoding 3-deoxy-D-arabino-heptulosonate-7-phosphate synthase and a gene tyrA$^{fbr}$ encoding chorismate mutase and prephenate dehydrogenase on an *E. coli* genome;

(b) knocking out a gene pheA encoding and fusing chorismate mutase/prephenate dehydratase, a gene trpE encoding an anthranilate synthetase subunit TrpE, a gene tyrR encoding a DNA binding transcription double regulator TyrR, a gene aroG$^{fbr}$ freely expressing and encoding 3-deoxy-D-arabino-heptulosonate-7-phosphate synthase, a gene tyrA$^{fbr}$ encoding chorismate mutase and prephenate dehydrogenase and a gene fpk encoding phosphoketolase on an *E. coli* genome;

(c) knocking out a gene pheA encoding and fusing chorismate mutase/prephenate dehydratase, a gene trpE encoding an anthranilate synthetase subunit TrpE, a gene tyrR encoding a DNA binding transcription double regulator TyrR, a gene poxB encoding pyruvate oxidase, a gene aroG$^{fbr}$ freely expressing and encoding 3-deoxy-D-arabino-heptulosonate-7-phosphate synthase, a gene tyrA$^{fbr}$ encoding chorismate mutase and prephenate dehydrogenase and a gene fpk encoding phosphoketolase on an *E. coli* genome;

(d) knocking out a gene pheA encoding and fusing chorismate mutase/prephenate dehydratase, a gene trpE encoding an anthranilate synthetase subunit TrpE, a gene tyrR encoding a DNA binding transcription double regulator TyrR, a gene poxB encoding pyruvate oxidase, a gene aroP encoding permease of an aromatic amino acid transporter AroP, a gene tyrP encoding a tyrosine and H (+) sympoter, a gene aroG$^{fbr}$ freely expressing and encoding 3-deoxy-D-arabino-heptulosonate-7-phosphate synthase, a gene tyrA$^{fbr}$ encoding chorismate mutase and prephenate dehydrogenase, a gene fpk encoding phosphoketolase and a gene yddG encoding an amino acid exportin YddG on an E. coli genome.

In one embodiment, the recombinant E. coli integrates a gene ppsA expressing phosphoenolpyruvate synthetase and a gene tktA encoding transketolase 1.

In one embodiment, the gene ppsA is integrated at a site ykgh-betA on the E. coli genome.

In one embodiment, the gene tktA is integrated at a site dadx-cvra on the E. coli genome.

In one embodiment, the gene ppsA and the gene tktA are initially expressed by a promoter $PJ_{231119}$.

In one embodiment, a heat induced expression vector pAP-B03 is used as an expression plasmid of the E. coli.

In one embodiment, the gene pheA has a nucleotide sequence set forth in SEQ ID NO:1.

In one embodiment, the gene trpE has a nucleotide sequence set forth in SEQ ID NO:2.

In one embodiment, the gene aroG$^{fbr}$ has a nucleotide sequence set forth in SEQ ID NO:3.

In one embodiment, the gene tyrA$^{fbr}$ has a nucleotide sequence set forth in SEQ ID NO:4.

In one embodiment, the gene tyrR has a nucleotide sequence set forth in SEQ ID NO:5.

In one embodiment, the gene ppsA has a nucleotide sequence set forth in SEQ ID NO:6.

In one embodiment, the gene tktA has a nucleotide sequence set forth in SEQ ID NO:7.

In one embodiment, the gene fpk has a nucleotide sequence set forth in SEQ ID NO:8.

In one embodiment, the gene poxB has a nucleotide sequence set forth in SEQ ID NO:9.

In one embodiment, the gene aroP has a nucleotide sequence set forth in SEQ ID NO:10.

In one embodiment, the gene tyrP has a nucleotide sequence set forth in SEQ ID NO:11.

In one embodiment, the gene yddG has a nucleotide sequence set forth in SEQ ID NO:12.

In one embodiment, the promoter $PJ_{231119}$ has a nucleotide sequence set forth in SEQ ID NO:101.

In one embodiment, the heat induced expression vector pAP-B03 plasmid is used for freely expressing the aroG$^{fbr}$, the fpk, the yddG and the tyrA$^{fbr}$.

In one embodiment, the heat induced expression vector pAP-B03 plasmid is recorded in the document "Zhou, H., Liao, X., Wang, T., Du, G., Chen, J., 2010. Enhanced L-phenylalanine biosynthesis by co-expression of pheA$^{fbr}$ and aroF$^{wt}$. Bioresource Technology. 101(11): 4151-4156.".

In one embodiment, E. coli K12, E. coli BL21, E. coli DH5α, E. coli JM109 or E. coli HG is used as the original strain.

In one embodiment, the strain E. coli HG is a strain WSH-Z06 (pAP-B03) recorded in the document "Zhou, H., Liao, X., Wang, T., Du, G., Chen, J., 2010. Enhanced L-phenylalanine biosynthesis by co-expression of pheA$^{fbr}$ and aroF$^{wt}$. Bioresource Technology. 101(11): 4151-4156.".

The present disclosure provides a method for producing L-tyrosine. The method includes using the recombinant E. coli to produce the L-tyrosine by fermentation.

In one embodiment, the recombinant E. coli is inoculated into a fermentation system, cultured at 32-34° C. for 3-12 h and fermented at 200-220 rpm at 36-40° C. for 48-60 h.

In one embodiment, the fermentation system includes 30-40 g/L glucose, 3-7 g/L $(NH_4)_2SO_4$, 1-5 g/L $KH_2PO_4$, 1-5 g/L $MgSO_4 \cdot 7H_2O$, 1-2 g/L sodium citrate, 0.5-1.5 g/L NaCl, 0.05-0.1 g/L vitamin $B_1$, 0.1-0.12 g/L $FeSO_4 \cdot 7H_2O$, 1-3 g/L yeast powder, 2-6 g/L peptone and 1-2 mL/L trace element nutrient solution (TES).

In one embodiment, the TES includes the following components: 2.0 g/L $Al_2(SO_4)_3 \cdot 18H_2O$, 0.75 g/L $CoSO_4 \cdot 7H_2O$, 2.5 g/L $CuSO_4 \cdot 5H_2O$, 0.5 g/L $H_3BO_3$, 24 g/L $MnSO_4 \cdot H_2O$, 2.5 g/L $NiSO_4 \cdot 6H_2O$ and 15 g/L $ZnSO_4 \cdot 7H_2O$.

The present disclosure provides application of the recombinant E. coli in production of L-tyrosine or a product containing L-tyrosine.

The Present Disclosure has the Following Beneficial Effects

1. According to the present disclosure, with E. coli as a host, in order to increase the carbon flux of a synthetic route for synthesis of tyrosine, a gene pheA encoding chorismate mutase-prephenate dehydratase (CM-PDT) in the E. coli is knocked out by a CRISPR/Cas9 gene editing method, aroG$^{fbr}$, tyrA$^{fbr}$, tktA and ppsA are freely expressed by a heat induced plasmid pAP-B03, a gene trpE encoding an anthranilate synthetase subunit trpE is further knocked out to block the synthesis of tryptophan, and a gene tyrR is knocked out to relieve a repression effect of a protein TyrR on key enzymes of a shikimic acid pathway. After fermentation for 48 h, 5.6 g/L tyrosine is accumulated in a shake flask.

2. In order to further improve the utilization of glucose, a gene fpk encoding phosphoketolase from Bifidobacterium adolescentis is heterologously expressed to directionally guide glucose to a shikimic acid pathway so as to increase precursor supply of the shikimic acid pathway, genes tktA and ppsA are integrated and expressed on an E. coli genome, and a strong promoter $PJ_{231119}$ is used to initiate gene expression. After fermentation for 48 h, 6.0 g/L L-tyrosine is accumulated in a shake flask.

3. An acetic acid pathway of E. coli is modified, and a gene poxB encoding pyruvate oxidase (PoxB) on the E. coli genome is knocked out to effectively reduce the production of acetic acid, so that the content of the L-tyrosine is increased to 6.2 g/L.

4. Genes aroP and tyrP are knocked out, an aromatic amino acid transport system of E. coli is modified by freely expressing an endogenous gene yddG of E. coli, then a gene fpk encoding phosphoketolase is freely expressed, the genes ppsA and tktA are integrated and expressed to increase precursor supply of the shikimic acid pathway, and then feedback inhibition of 3-deoxy-D-arabino-heptulosonate-7-phosphate synthase, chorismate mutase and prephenate dehydrogenase is relieved by expressing anti-feedback genes of aroG$^{fbr}$ and tyrA$^{fbr}$, so that the carbon flux of the shikimic acid pathway is increased. A repression effect of a protein TyrR on key enzymes of the shikimic acid pathway is relieved by knocking out a gene tyrR, and partial side reactions of the shikimic acid pathway are blocked by knocking out genes trpE and pheA, so that the synthesis flux of tyrosine is increased. Finally, an endogenous gene poxB is knocked out to realize transformation of an acetic acid pathway, so that stable fermentation performance at high glucose concentration is realized. When an engineered strain of E. coli obtained by the method of the present disclosure is subjected to induced fermentation for 55 h, the content of L-tyrosine in a fermentation liquid is as high as 80.5 g/L, and the production intensity reaches 1.46 g/L/h, so that a new idea is provided for industrial production of L-tyrosine.

DETAILED DESCRIPTION (I) Culture Media

Figure 1:
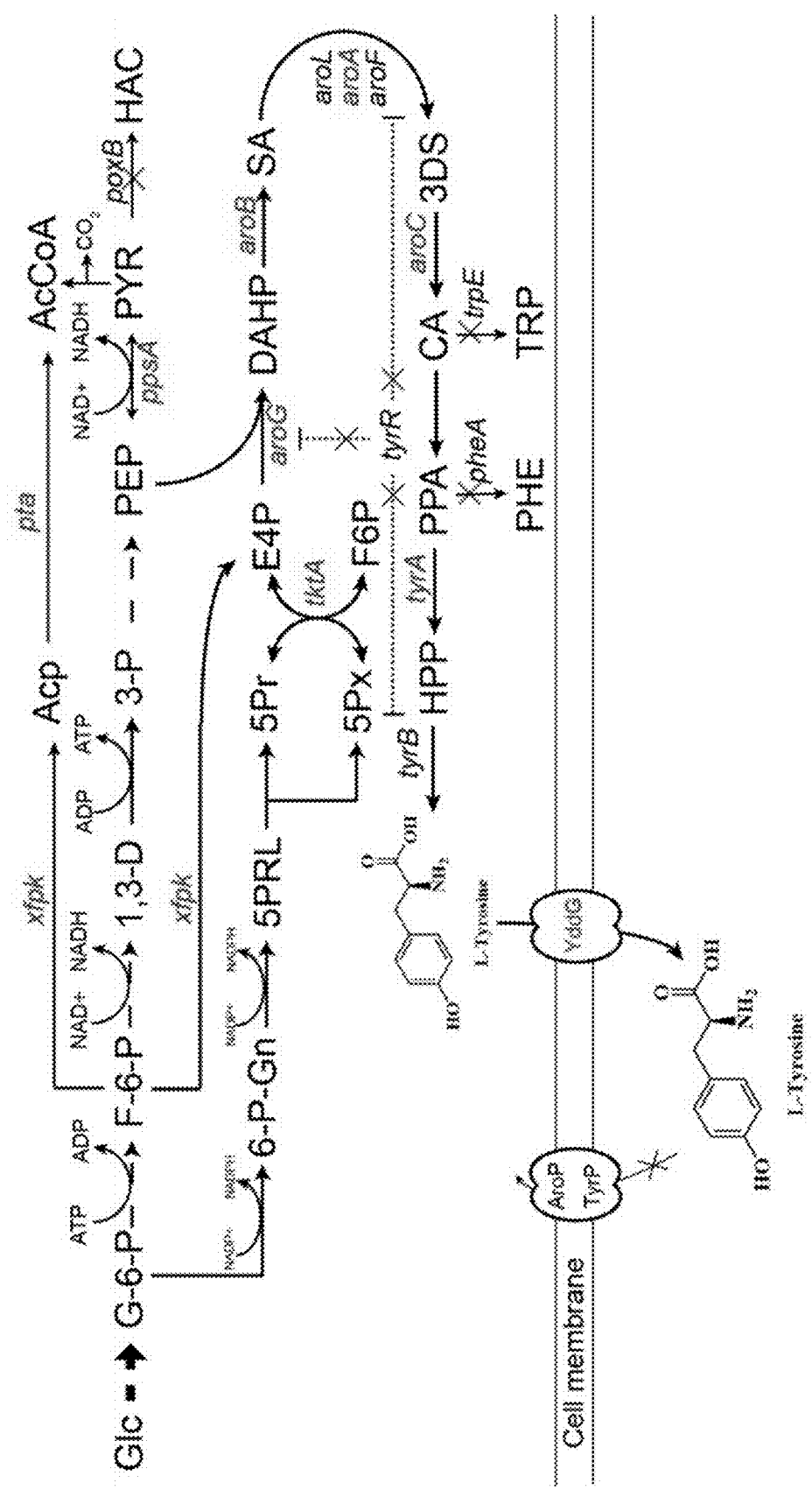
FIG. 1 is a diagram showing synthesis of L-tyrosine in E. coli.

A seed culture medium (LB) includes: 10 g/L peptone, 5 g/L a yeast extract and 5 g/L sodium chloride; and 2% (mass fraction) agar powder was added into a solid culture medium.

A fermentation culture medium (1 L) includes: 35 g of glucose, 5 g of $(NH_4)_2SO_4$, 3 g of $K_2HPO_4 \cdot 3H_2O$, 3 g of $MgSO_4 \cdot 7H_2O$, 1.5 g of sodium citrate, 1 g of NaCl, 0.075 g of vitamin $B_1$, 0.1125 g of $FeSO_4 \cdot 7H_2O$, 2 g of yeast powder, 4 g of peptone and 1.5 mL of a trace element nutrient solution (TES), and appropriate amounts of antibiotics were added as required. 12 g of calcium carbonate was added into a conical flask to control the pH value; and the TES includes: 2.0 g/L $Al_2(SO_4)_3 \cdot 18H_2O$, 0.75 g/L $CoSO_4 \cdot 7H_2O$, 2.5 g/L $CuSO_4 \cdot 5H_2O$, 0.5 g/L $H_3BO_3$, 24 g/L $MnSO_4 \cdot H_2O$, 2.5 g/L $NiSO_4 \cdot 6H_2O$ and 15 g/L $ZnSO_4 \cdot 7H_2O$.

(II) PCR Reaction System and Amplification Conditions

1 µL (10 µM) of a forward primer, 1 µL (10 µM) of a reverse primer, 10-50 ng of template DNA and 25 µL of 2×Phanta Max Master Mix, and double distilled water added to 50 µL. Amplification conditions include: pre-denaturation at 95° C. for 3 min, followed by 30 cycles (at 95° C. for 15 s, at 55° C. for 15 s) and at 72° C. for 15 s) and continuous extension at 72° C. for 5 min.

(III) Preparation of E. coli Competent Cells

E. coli K12 in a glycerol tube was streaked on a corresponding LB plate and cultured overnight at 37° C. (for about 12 h). 12 h later, monoclone is picked, inoculated into a 50 mL shake flask containing 5 mL of an LB culture medium and cultured at 220 rpm at 37° C. until an $OD_{600}$ value was 0.6-0.8. A bacterial solution was transferred to a 50 mL centrifuge tube, placed on ice for about 15 min and centrifuged at 4,000 rpm at 4° C. for 5 min to remove a supernatant. 5 mL of a solution A was added for resuspension, and centrifugation was performed at 4,000 rpm at 4° C. for 5 min to remove a supernatant. Then, 5 mL of a solution B was added to resuspend the bacteria, and a resulting product was packaged in 100 µL/part and store at −80° C.

(IV) Transformation of E. coli

E. coli competent cells were thawed on ice. 10 µL of a recombinant product (50 ng of plasmid) was added into 100 µL of the competent cells, evenly mixed by flicking, and subjected to standing on ice for 30 min. A resulting mixture was subjected to heat shock in a water bath pot at 42° C. for 45 s, followed by standing on ice for 2 min. 1 mL of an LB culture medium was added, and the bacteria were shaken at 220 rpm at 37° C. for 60 min. Then, centrifugation was performed at 4,500 rpm for 2 min to remove a supernatant. The bacteria were resuspended with the remaining culture medium and then coated on a resistant plate.

(V) Determination of L-Tyrosine by High Performance Liquid Chromatography (HPLC)

After completion of fermentation, 1 mL of a fermentation liquid was taken, diluted to an appropriate multiple with 3 M hydrochloric acid, violently shaken and uniformly mixed, followed by centrifugation at 14,000 rpm for 10 min. A supernatant was taken and filtered with a 0.22 µm inorganic filter membrane, and a product was detected by a high performance liquid chromatograph LC-20A of Shimadzu. A Thermo Fisher C18 chromatographic column (4.6 mm×250 mm, 5 µm) was used for chromatographic separation; the temperature of a column oven was set to 30° C.; the injection volume was 10 µL; mobile phases were as follows: phase A: 0.1 M sodium acetate (the pH was adjusted to 4.5 with glacial acetic acid), and phase B: pure methanol; the total flow rate was 1 mL/min; the volume percentage was 90% and 10%, respectively; and the wavelength of a detector was 280 nm.

(VI) Plasmids

A plasmid pAP-B03 involved in the following examples is recorded in the document "Zhou, H., Liao, X., Wang, T., Du, G., Chen, J., 2010. Enhanced L-phenylalanine biosynthesis by co-expression of pheA$^{fbr}$ and aroF$^{wt}$. Bioresource Technology. 101(11): 4151-4156.". Plasmids pCas and p-Target involved in the following examples are recorded in the document "Jiang, Y., Chen, B., Duan, C., Sun, B., Yang, J., Yang, S., 2015. Multigene editing in the Escherichia coli genome via the CRISPR-Cas9 system. Applied and Environmental Microbiology. 81(7): 2506-2514.". A recombinant plasmid pCDF-aroG$^{fbr}$-tyrA$^{fbr}$ involved in the following examples is recorded in the document "Wu, J., Zhou, T., Du, G., Zhou, J., Chen, J., 2014. Modular optimization of heterologous pathways for de novo synthesis of (2S)-naringenin in Escherichia coli. PloS One. 9(7): 1-9.". A strain E. coli HG involved in the following examples is a strain WSH-Z06 (pAP-B03) recorded in the document "Zhou, H., Liao, X., Wang, T., Du, G., Chen, J., 2010. Enhanced L-phenylalanine biosynthesis by co-expression of pheA$^{fbr}$ and aroF$^{wt}$. Bioresource Technology. 101(11): 4151-4156.", which is named as E. coli HG in the present disclosure.

(VII) Information of Strains as Shown in Table 1

TABLE 1

Strains and genes involved in the present disclosure

| Strain name | Genotype |
| --- | --- |
| E. coli HG0 | E. coli HG eliminate pAP-pheA$^{fbr}$-aroF$^{fbr}$ |
| E. coli HGA | E. coli HG0 ΔpheA containing pAP-aroG$^{fbr}$-tyrA$^{fbr}$-ppsA-tktA |
| E. coli HGB | E. coli HG0 ΔpheAΔtrpE containing pAP-aroG$^{fbr}$-tyrA$^{fbr}$-ppsA-tktA |
| E. coli HGC | E. coli HG0 ΔpheAΔtrpEΔtyrR containing pAP-aroG$^{fbr}$-tyrA$^{fbr}$-ppsA-tktA |
| E. coli HGD0 | E. coli HG0 ΔpheAΔtrpEΔtyrR dadx-cvra::tktA |
| E. coli HGE | E. coli HGD0 ykgh-betA::ppsA containing pAP-aroG$^{fbr}$-tyrA$^{fbr}$-fpk |

TABLE 1-continued

Strains and genes involved in the present disclosure

| Strain name | Genotype |
|---|---|
| E. coli HGF | E. coli HGE ΔpoxB containing pAP-aroG$^{fbr}$-tyrA$^{fbr}$-fpk |
| E. coli HGG | E. coli HGF0 ΔaroP containing pAP-aroG$^{fbr}$-tyrA$^{fbr}$-fpk |
| E. coli HGH0 | E. coli HGF0 ΔaroPΔtyrP |
| E. coli HGH | E. coli HGF0 ΔaroPΔtyrP containing pAP-aroG$^{fbr}$-yddG-tyrA$^{fbr}$-fpk |

Example 1: Construction of Recombinant *E. coli* for Synthesis of L-Tyrosine (1) Preparation of an Engineered Strain HGA0

*E. coli* HG stored in a laboratory was continuously subjected to passage culture at 42° C. for removing a plasmid to obtain a plasmid-free strain HG0. A plasmid pCas was transformed into chemically transformed competent cells of the *E. coli* HG0; monoclone obtained by transformation is picked into a 4 mL of an LB culture medium containing 50 μg/mL kanamycin and cultured at 30° C. for 12 h; then a bacterial solution with a volume ratio of 2% was inoculated into 50 mL of an LB culture medium; and kanamycin with a final concentration of 50 μg/mL and a 10 mM arabinose solution were added. A mixed solution was cultured at 220 rpm at 30° C. for 4-6 h, and when the optical density (OD) value was 0.6, the bacterial solution was transferred to a 50 mL centrifuge tube and subjected to standing on ice for 15 min. Centrifugation was performed at 4,000 rpm at 4° C. for 10 min to remove a supernatant, and 10 mL of 10% glycerol was added for resuspension; the operation was repeated twice, and a resulting product was packaged at 100 μL/part and stored at −80° C. to obtain electrically transformed competent cells of *E. coli* HG0 containing a plasmid pCas, named as *E. coli* HG0-pCas.

The *E. Coli* HG0 was selected as an original strain for production of L-tyrosine by fermentation. First, according to a synthetic route of L-tyrosine shown in FIG. 1, in order to increase the carbon flux of a synthetic route for synthesis of tyrosine, a gene pheA encoding chorismate mutase-prephenate dehydratase (CM-PDT) in *E. coli* was knocked out by a CRISPR/Cas9 gene editing method. With an *E. coli* K12 genome as a template, an upstream homologous arm U1 and a downstream homologous arm D1 of the gene pheA were amplified with primer pairs F11/R11 and F12/R12, respectively, and fragments were purified. With purified fragments U1 and D1 as templates, a knockout box UD1 was obtained by amplification with a primer pair F11/R12, and fragments were purified. In order to obtain pTarget-pheA for knocking out the pheA, amplification was performed with a primer pair F13/R13 with p-Target stored in a laboratory as a template, and fragments were purified. A purified fragment pTarget-pheA was transformed into *E. coli* JM109, and a plasmid was extracted and sequenced for verification to obtain a correct recombinant vector pTarget-pheA.

400 ng of the recombinant vector pTarget-pheA and 1,200 ng of the knockout box UD1 were added into the electrically transformed competent cells of *E. coli* HG0-pCas, and a mixture was subjected to standing on ice for 10 min, transferred into a 1 mm electroporation cuvette precooled for 10 min and then subjected to electric shock at a voltage of 1.8 kv. After completion of the electric shock, 1 mL of an LB liquid culture medium was added and cultured at 30° C. for 1.5 h. Bacterial colonies were subjected to PCR verification with a primer pair F14/R14, and the verified monoclone loses the pTarget-pheA and the pCas9 to obtain an engineered strain of *E. coli* HGA0.

(2) Preparation of Overexpression Plasmids pAP-aroG$^{fbr}$-tyrA$^{fbr}$ and pAP-aroG$^{fbr}$-tyrA$^{fbr}$-ppsA-tktA and an Engineered Strain HGA A heat induced plasmid framework was obtained from a plasmid pAP-B03 with a primer pair F113/R113, including a kanamycin gene, a promoter $P_R P_L$ (obtained with a primer pair F116/R116) and a replicator p15A. Genes aroG$^{fbr}$ and tyrA$^{fbr}$ were obtained from a plasmid pCDF-aroG$^{fbr}$-tyrA$^{fbr}$ with primer pairs F114/R114 and F117/R117, respectively. A gene tktA and a gene ppsA were obtained from an *E. coli* genome by amplification with primer pairs F115/R115 and F118/R118, respectively. The obtained heat induced plasmid framework was assembled with the target genes aroG$^{fbr}$, tyr A$^{fbr}$, tktA and ppsA by a GIBSON ASSEMBLY® method (a cloning method that joins DNA fragments together without the need for restriction enzymes) to obtain plasmids pAP-aroG$^{fbr}$-tyrA$^{fbr}$ and pAP-aroG$^{fbr}$-tyrA$^{fbr}$-ppsA-tktA.

The recombinant vector pAP-aroG$^{fbr}$-tyrA$^{fbr}$-ppsA-tktA was transformed into the *E. coli* HGA0 to obtain an engineered strain HGA.

(3) Preparation of Engineered Strains HGB0 and HGB

With the engineered strain HGA0 as an original strain, electrically transformed competent cells HGA0-pCas of HGA0 containing a plasmid pCas were constructed by the same method. A gene trpE was knocked out by the same method to block the synthesis of tryptophan. With an *E. coli* K12 genome as a template, upstream and downstream homologous arms of the trpE were amplified with primer pairs F15/R15 and F16/R16, respectively, and a knockout box UD2 was obtained by amplification with a primer pair F15/R16. p-Target was amplified with a primer F17/R17 to prepare a recombinant vector pTarget-trpE. The knockout box UD2 and the recombinant vector pTarget-trpE were electrically transformed into the HGA0-pCas. Bacterial colonies were subjected to PCR verification with a primer pair F18/R18, and the verified monoclone loses the pTarget-trpE and the pCas9 to obtain an engineered strain HGB0.

The recombinant vector pAP-aroG$^{fbr}$-tyrA$^{fbr}$-ppsA-tktA was transformed into the *E. coli* HGB0 to obtain an engineered strain HGB.

(4) Preparation of Engineered Strains HGC0 and HGC

With the engineered strain HGB0 as an original strain, electrically transformed competent cells HGB0-pCas of HGB0 containing a plasmid pCas were constructed by the same method. With an *E. coli* K12 genome as a template, a gene tyrR was knocked out by the same method to relieve a repression effect of accumulation of amino acids on key enzymes of a shikimic acid pathway, upstream and downstream homologous arms of the tyrR were amplified with primer pairs F19/R19 and F110/R110, respectively, and a knockout box UD3 was obtained by amplification with a primer pair F19/R110. p-Target was amplified with a primer pair F111/R111 to prepare a recombinant vector pTarget-tyrR. The knockout box UD3 and the recombinant vector pTarget-tyrR were electrically transformed into the HGB0-pCas. Bacterial colonies were subjected to PCR verification with a primer pair F112/R112, and the verified monoclone loses the pTarget-tyrR and the pCas9 to obtain an engineered strain HGC0.

The recombinant vector pAP-aroG$^{fbr}$-tyrA$^{fbr}$-ppsA-tktA was transformed into the E. coli HGC0 to obtain an engineered strain HGC.

The engineered strain HGC was inoculated into 50 mL of a seed culture medium and cultured at 220 rpm at 37° C. for 12 h to obtain a seed liquid. Then, the seed liquid was inoculated into a fermentation culture medium containing kanamycin with a final concentration of 50 μg/mL at an inoculation amount of 2% (v/v) and cultured at 220 rpm at 33° C. for 3 h, and the temperature was changed to 38° C. Synthesis of L-tyrosine was induced at 220 rpm at 38° C., fermentation was performed for 48 h, and 5.6 g/L tyrosine was accumulated in a shake flask.

All primer sequences are listed in Table 2.

TABLE 2

Primer sequences

| Primer name | Primer sequence | |
|---|---|---|
| F11 | cgtctcgccaaactggaaaaatgg | SEQ ID NO: 13 |
| R11 | cttttcaccccgatttgggaggccttattg | SEQ ID NO: 14 |
| F12 | ctcccaaatcggggtgaaaaggtgccggatgatgtgaatcatcc | SEQ ID NO: 15 |
| R12 | caatggtttctggagcaaattcaggtctg | SEQ ID NO: 16 |
| F13 | atataccgaaagtacgtctggttttagagctagaaatagcaagttaaaataaggctag | SEQ ID NO: 17 |
| R13 | cagacgtactttcggtatatactagtattatacctaggactgagctagctg | SEQ ID NO: 18 |
| F14 | ccagcaaacaaatggaaattactccgg | SEQ ID NO: 19 |
| R14 | gtctggtgtgatggacgtaaaccg | SEQ ID NO: 20 |
| F15 | ccaggcgttcaattaaggtttgcg | SEQ ID NO: 21 |
| R15 | gtttttatctcgccgaactgcgtcacgatcttgac | SEQ ID NO: 22 |
| F16 | gacgcagttcggcgagataaaaacagaaatcagggcag | SEQ ID NO: 23 |
| R16 | cgactctcgaactgctaacctgc | SEQ ID NO: 24 |
| F17 | attgccggaacacgcccacggttttagagctagaaatagcaagttaaaataagg | SEQ ID NO: 25 |
| R17 | cgtgggcgtgttccggcaatactagtattatacctaggactgagctagctg | SEQ ID NO: 26 |
| F18 | ccaggagaaagcatcagcacc | SEQ ID NO: 27 |
| R18 | gcaatcagatacccagcccg | SEQ ID NO: 28 |
| F19 | cggaatcaacgttgatgattgcgg | SEQ ID NO: 29 |
| R19 | aggcatattcgcacttcggcgtaaagatatccg | SEQ ID NO: 30 |
| F110 | gccgaagtgcgaatatgcctgatggtgcaacacc | SEQ ID NO: 31 |
| R110 | gatctgtctgacgtcaccctcg | SEQ ID NO: 32 |
| F111 | ccacgggacagtacgcacatgttttagagctagaaatagcaagttaaaataag | SEQ ID NO: 33 |
| R111 | atgtgcgtactgtcccgtggactagtattatacctaggactgagctagctg | SEQ ID NO: 34 |
| F112 | gtccagccagttttagatgcccag | SEQ ID NO: 35 |
| R112 | gttacagtcgccaattccatccc | SEQ ID NO: 36 |
| F113 | gaagaaataaccggcgttcagcctgtgc | SEQ ID NO: 37 |
| R113 | cgttctgataattcatgatctttagctgtcttggtttgccc | SEQ ID NO: 38 |
| F114 | atgaattatcagaacgacgatttacgcatc | SEQ ID NO: 39 |
| R114 | gtgaggacatggtatatctcctttttacccgcgacgcgcttttac | SEQ ID NO: 40 |
| F115 | gggtaaaaggagatataccatgtcctcacgtaaagagcttgcc | SEQ ID NO: 41 |
| R115 | gtaggtgagttacagcagttcttttgctttcgcaac | SEQ ID NO: 42 |

TABLE 2-continued

Primer sequences

| Primer name | Primer sequence | |
|---|---|---|
| F116 | gcaaaagaactgctgtaactcacctaccaaacaatgcccc | SEQ ID NO: 43 |
| R116 | gcaaccattggatcccaatgcttcgtttcg | SEQ ID NO: 44 |
| F117 | ggatccaatggttgctgaattgaccgcattac | SEQ ID NO: 45 |
| R117 | gttggacatggtatatctccttttactggcgattgtcattcgcc | SEQ ID NO: 46 |
| F118 | gccagtaaaaggagatataccatgtccaacaatggctcgtcac | SEQ ID NO: 47 |
| R118 | ggctgaacgccggttatttcttcagttcagccaggcttaacc | SEQ ID NO: 48 |

Example 2: Exogenous Introduction of Fpk to Improve Synthesis of L-Tyrosine

In order to improve the utilization of glucose, fpk from *Bifidobacterium adolescentis* was heterologously expressed to directionally guide glucose to a shikimic acid pathway so as to increase precursor supply of the shikimic acid pathway. In order to prevent too long plasmids from affecting gene expression efficiency, genes ppsA and tktA and a strong promoter $PJ_{231119}$ were linked for integration on an *E. coli* genome.

(1) Preparation of an Engineered Strain HGD0

With the engineered strain HGC0 constructed in Example 1 as an original strain, electrically transformed competent cells HGC0-pCas of HGC0 containing a plasmid pCas were constructed by the same method. A gene tktA was integrated by the same gene knockout method. With an *E. coli* K12 genome as a template, the gene tktA was amplified with a primer pair F23/R23, and upstream and downstream homologous arms of dadx-cvra were amplified with primer pairs F24/R24 and F25/R25, respectively. With the gene tktA and the upstream and downstream homologous arms of dadx-cvra as templates, a knock-in box UTD was obtained by amplification of the tktA and the upstream and downstream homologous arms with a primer pair F24/R25. p-Target was amplified with a primer pair F26/R26 to prepare a recombinant vector pTarget-dadx-cvra. The knock-in box UTD and the recombinant vector pTarget-dadx-cvra were electrically transformed into the HGC0-pCas. Bacterial colonies were subjected to PCR verification with a primer pair F27/R27, and the verified monoclone loses the pTarget-dadx-cvra and the pCas9 to obtain an engineered strain HGD0.

(2) Preparation of an Overexpression Plasmid pAP-aroG$^{fbr}$-tyrA$^{fbr}$-Fpk and Engineered Strains HGE0 and HGE Electrically transformed competent cells HGD0-pCas of HGD0 containing a plasmid pCas were constructed by the same method. A gene ppsA was integrated by the same method. With an *E. coli* K12 genome as a template, the gene ppsA was amplified with a primer pair F28/R28, upstream and downstream homologous arms of ykgh-betA were amplified with primer pairs F29/R29 and F210/R210, respectively, and a knock-in box UPD was obtained by amplification of the ppsA and the upstream and downstream homologous arms with a primer pair F29/R210. p-Target was amplified with a primer pair F211/R211 to prepare a recombinant vector pTarget-ykgh-betA. The knock-in box UPD and the recombinant vector pTarget-ykgh-betA were electrically transformed into the HGD0-pCas. Bacterial colonies were subjected to PCR verification with a primer pair F212/R212, and the verified monoclone loses the pTarget-ykgh-betA and the pCas9 to obtain an engineered strain HGE0.

With synthetic fpk as a template, amplification was performed with a primer pair F21/R21, followed by purification and recovery. With the recombinant vector pAP-aroG$^{fbr}$-tyrA$^{fbr}$ constructed in Example 1 as a template, amplification was performed with a primer pair F22/R22, and fragments were recovered. A fragment fpk and the vector pAP-aroG$^{fbr}$-tyrA$^{fbr}$ skeleton were reconstructed by a GIBSON ASSEMBLY® method (a cloning method that joins DNA fragments together without the need for restriction enzymes) to obtain a recombinant vector, the recombinant vector was transformed into *E. coli* JM109, and a plasmid was extracted and sequenced for verification to obtain a correct recombinant vector pAP-aroG$^{fbr}$-tyrA$^{fbr}$-fpk.

The engineered strain HGE was inoculated into 50 mL of a seed culture medium and cultured at 220 rpm at 37° C. for 12 h to obtain a seed liquid. Then, the seed liquid was inoculated into a fermentation culture medium containing kanamycin with a final concentration of 50 µg/mL at an inoculation amount of 2% (v/v), and cultured at 220 rpm at 33° C. for 3 h, and the temperature was changed to 38° C. Synthesis of L-tyrosine was induced at 220 rpm at 38° C., fermentation was performed for 48 h, and 6.0 g/L L-tyrosine was accumulated in a shake flask.

All primer sequences are listed in Table 3.

TABLE 3

Primer sequences

| Primer name | Primer sequence | |
|---|---|---|
| F21 | ggtaaaaggagatataccatgactaaccctgtaatcggtactcc | SEQ ID NO: 49 |
| R21 | gtttggtaggtgagttattcattgtcaccagcagtagcagc | SEQ ID NO: 50 |
| F22 | ggtgacaatgaataactcacctaccaaacaatgcccc | SEQ ID NO: 51 |

TABLE 3-continued

Primer sequences

| Primer name | Primer sequence | |
|---|---|---|
| R22 | cagggttagtcatggtatatctccttttacccgcgacgcgcttttactgcattc | SEQ ID NO: 52 |
| F23 | ttgacagctagctcagtcctaggtataatactagtaaagaggagaaaaagcttatgtcctcacgtaaagagcttgc | SEQ ID NO: 53 |
| R23 | ttacagcagttcttttgctttcgcaac | SEQ ID NO: 54 |
| F24 | gtgatatcgccaataccggattacg | SEQ ID NO: 55 |
| R24 | ggactgagctagctgtcaatgcggtgagttcaggttccgg | SEQ ID NO: 56 |
| F25 | gcaaaagaactgctgtaacaggcgttctacataaaacgcttacgc | SEQ ID NO: 57 |
| R25 | ggcgatgtgttgtgtgtaattgg | SEQ ID NO: 58 |
| F26 | ggcgaagaatatcatccatggttttagagctagaaatagcaagttaaaataagg | SEQ ID NO: 59 |
| R26 | catggatgatattcttcgccactagtattatacctaggactgagctagctg | SEQ ID NO: 60 |
| F27 | cgcattttgactgggttcggc | SEQ ID NO: 61 |
| R27 | gcggcactgtttcgtgataacc | SEQ ID NO: 62 |
| F28 | ttgacagctagctcagtcctaggtataatactagtaaagaggagaaaaagcttatgtccaacaatggctcgtcac | SEQ ID NO: 63 |
| R28 | gattgagagttttatttcttcagttcagccaggcttaac | SEQ ID NO: 64 |
| F29 | gtatctcatcgagaacttgcctgcc | SEQ ID NO: 65 |
| R29 | gactgagctagctgtcaaaccgttccagagagggggacc | SEQ ID NO: 66 |
| F210 | gaagaaataaaactctcaatctgatcggttcctgc | SEQ ID NO: 67 |
| R210 | gtgcggattaaatcccgcgac | SEQ ID NO: 68 |
| F211 | ggtgaaaacgactatcacgggttttagagctagaaatagcaagttaaaataagg | SEQ ID NO: 69 |
| R211 | ccgtgatagtcgttttcaccactagtattatacctaggactgagctagctg | SEQ ID NO: 70 |
| F212 | cggatacaatgaccagttcctgg | SEQ ID NO: 71 |
| R212 | Cggtttccagtgccacgtc | SEQ ID NO: 72 |

Example 3: Modification of Acetic Acid Pathway to Improve Utilization of Glucose When the HGE strain constructed in Example 2 was fermented in a shake flask, it was found that the content of acetic acid accumulated in the shake flask was 1.2 g/L within 48 h, resulting in serious waste of carbon resources. Therefore, an acetic acid pathway of *E. coli* was modified. A gene poxB encoding pyruvate oxidase (PoxB) in *E. coli* was knocked out.

With an *E. coli* K12 genome as a template, an upstream homologous arm U1 and a downstream homologous arm D1 of the gene poxB were amplified with primer pairs F31/R31 and F32/R32, respectively, and fragments were purified. With purified fragments U1 and D1 as templates, a knockout box UD1 was obtained by amplification with a primer pair F31/R32, and fragments were purified. In order to obtain pTarget-poxB for knocking out the poxB, amplification was performed with a primer pair F33/R33 with p-Target stored in a laboratory as a template, and fragments were purified. A purified fragment was transformed into *E. coli* JM109, and a plasmid was extracted and sequenced for verification to obtain a correct recombinant vector pTarget-poxB.

With the engineered strain HGE as an original strain, electrically transformed competent cells HGE-pCas of HGE containing a plasmid pCas were constructed by the same method. A gene poxB of *E. coli* HGE was knocked out by the same experimental method in Example 1. Bacterial colonies were subjected to PCR verification with a primer pair F34/R34, and the verified monoclone loses the pTarget-poxB and the pCas9 to obtain an engineered strain HGF0.

The recombinant vector pAP-aroG$^{fbr}$-tyrA$^{fbr}$-fpk in Example 2 was transformed into the *E. coli* HGF0 to obtain an engineered strain HGF.

The engineered strain HGF was inoculated into 50 mL of a seed culture medium and cultured at 220 rpm at 37° C. for 12 h to obtain a seed liquid. Then, the seed liquid was inoculated into a fermentation culture medium containing kanamycin with a final concentration of 50 μg/mL at an inoculation amount of 2% (v/v), and cultured at 220 rpm at 33° C. for 3 h, and the temperature was changed to 38° C. Synthesis of L-tyrosine was induced at 220 rpm at 38° C., fermentation was performed for 48 h, and 6.2 g/L L-tyrosine was accumulated in a shake flask, where the accumulation content of acetic acid was only 0.45 g/L, which was effectively reduced by 62.5%.

All primer sequences are listed in Table 4.

TABLE 4

Primer sequences

| Primer name | Primer sequence | |
|---|---|---|
| F31 | ggcaacactttgccgttgtgg | SEQ ID NO: 73 |
| R31 | cataatcgccgaactggcgaaaacaaactggc | SEQ ID NO: 74 |
| F32 | tcgccagttcggcgattatgcgagaaccaaatcc | SEQ ID NO: 75 |
| R32 | cgatgagtggcgtaactatccgg | SEQ ID NO: 76 |
| F33 | ggtgaaaatagcgtcatcgggttttagagctagaaatagcaagttaaaat aagg | SEQ ID NO: 77 |
| R33 | ccgatgacgctattttcaccactagtattataccttaggactgagctagctg | SEQ ID NO: 78 |
| F34 | gtcaacatgcagcgccagatt | SEQ ID NO: 79 |
| R34 | gatctacaacgtgcgtacgcc | SEQ ID NO: 80 |

Example 4: Modification of Aromatic Amino Acid Transport System (1) Preparation of Engineered Strains HGG0 and HGG Through determination of the intracellular content of tyrosine in the strain HGF in Example 3, it was found that the intracellular concentration of tyrosine in the HGF was 972.7% higher than that of wild-type $E.\ coli$ K12 as a control group. Therefore, an aromatic amino acid transport system of the HGF was modified. A gene aroP encoding permease of an aromatic amino acid transporter AroP in $E.\ coli$ was knocked out. With an $E.\ coli$ K12 genome as a template, an upstream homologous arm U1 and a downstream homologous arm D1 of the gene aroP were amplified with primer pairs F41/R41 and F42/R42, respectively, and fragments were purified. With purified fragments U1 and D1 as templates, a knockout box UD1 was obtained by amplification with a primer pair F41/R42, and fragments were purified. In order to obtain pTarget-aroP for knocking out the aroP, amplification was performed with a primer pair F43/R43 with p-Target stored in a laboratory as a template, and fragments were purified. A purified fragment was transformed into $E.\ coli$ JM109, and a plasmid was extracted and sequenced for verification to obtain a correct recombinant vector pTarget-aroP.

With the engineered strain HGF0 as an original strain, electrically transformed competent cells HGF0-pCas of HGF0 containing a plasmid pCas were constructed by the same method. A gene aroP of $E.\ coli$ HGF0 was knocked out by the same experimental method in Example 1. Bacterial colonies were subjected to PCR verification with a primer pair F44/R44, and the verified monoclone loses the pTarget-aroP and the pCas9 to obtain an engineered strain of $E.\ coli$ HGG0.

The recombinant vector pAP-aroG$^{fbr}$-tyrA$^{fbr}$-fpk in Example 2 was transformed into the $E.\ coli$ HGG0 to obtain an engineered strain HGG.

(2) Preparation of Overexpression Plasmid pAP-aroG$^{fbr}$-yddG-tyrA$^{fbr}$-Fpk and Engineered Strains HGH0 and HGH A gene tyrP was knocked out by the same method to block the synthesis of a tyrosine specific transport protein. With the engineered strain HGG0 as an original strain, electrically transformed competent cells HGG0-pCas of HGG0 containing a plasmid pCas were constructed by the same method. A gene tyrP was knocked out by the same method to block the synthesis of tryptophan. With an $E.\ coli$ K12 genome as a template, upstream and downstream homologous arms of the tyrP were amplified with primer pairs F45/R45 and F46/R46, respectively, and a knockout box UD1 was obtained by amplification with a primer pair F45/R46. p-Target was amplified with a primer pair F47/R47 to prepare a recombinant vector pTarget-tyrP. The knockout box UD1 and the recombinant vector pTarget-tyrP were electrically transformed into the HGG0-pCas. Bacterial colonies were subjected to PCR verification with a primer pair F48/R48, and the verified monoclone loses the pTarget-tyrP and the pCas9 to obtain an engineered strain HGH0.

With an $E.\ coli$ K12 genome as a template, a fragment yddG was amplified with a primer pair F49/R49. With the vector pAP-aroG$^{fbr}$-tyrA$^{fbr}$-fpk as a template, amplification was performed with a primer pair FP410/RP410, and a product was purified. A fragment yddG and the vector pAP-aroG$^{fbr}$-tyrA$^{fbr}$-fpk skeleton were reconstructed by a GIBSON ASSEMBLY® method (a cloning method that joins DNA fragments together without the need for restriction enzymes) to obtain a recombinant vector, the recombinant vector was transformed into $E.\ coli$ JM109, and a plasmid was extracted and sequenced for verification to obtain a correct recombinant vector pAP-aroG$^{fbr}$-yddG-tyrA$^{fbr}$-fpk. The recombinant vector pAP-aroG$^{fbr}$-yddG-tyrA$^{fbr}$-fpk was transformed into the $E.\ coli$ HGH0 to obtain an engineered strain HGH.

The engineered strain HGH was inoculated into 50 mL of a seed culture medium and cultured at 220 rpm at 37° C. for 12 h to obtain a seed liquid. Then, the seed liquid was inoculated into a fermentation culture medium containing kanamycin with a final concentration of 50 μg/mL at an inoculation amount of 2% (v/v), and cultured at 220 rpm at 33° C. for 3 h, and the temperature was changed to 38° C. Synthesis of L-tyrosine was induced at 220 rpm at 38° C., fermentation was performed for 48 h, and 6.9 g/L tyrosine was accumulated in a shake flask.

All primer sequences are listed in Table 5.

TABLE 5

Primer sequences

| Primer name | Primer sequence | |
|---|---|---|
| F41 | cgtgagtatttgcgtgagctgc | SEQ ID NO: 81 |
| R41 | acgaggtttctctctctacgccctcacccg | SEQ ID NO: 82 |
| F42 | cgtagagagagaaacctcgtgcggtggttg | SEQ ID NO: 83 |
| R42 | ggtcttaccaatttcatgtctgtgacg | SEQ ID NO: 84 |
| F43 | aatcaccacaaagaatacgggttttagagctagaaatagcaagttaaaataagg | SEQ ID NO: 85 |
| R43 | cagctagctcagtcctaggtataatactagtaatcaccacaaagaatacgg | SEQ ID NO: 86 |
| F44 | ttggcgcaggtaaagttcgt | SEQ ID NO: 87 |
| R44 | tgttttgccagttcgcgttc | SEQ ID NO: 88 |
| F45 | gcggcgaaggtctgtattttatcga | SEQ ID NO: 89 |
| R45 | ctatctgagctttcttctgtcctgacgatctttatgag | SEQ ID NO: 90 |
| F46 | cgtcaggacagaagaaagctcagatagcctcaaattccttattgggtgc | SEQ ID NO: 91 |
| R46 | ctggcttttcaacatatggccgatac | SEQ ID NO: 92 |
| F47 | agaaaatatatgccaccagggttttagagctagaaatagcaagttaaaataagg | SEQ ID NO: 93 |
| R47 | cagctagctcagtcctaggtataatactagtagaaaatatatgccaccagg | SEQ ID NO: 94 |
| F48 | gagcagcatgaagaagagaaactgttc | SEQ ID NO: 95 |
| R48 | ggcgtcagagaaagagatgacgc | SEQ ID NO: 96 |
| F49 | ggtaaaaggagatataccatgacacgacaaaaagcaacgc | SEQ ID NO: 97 |
| R49 | gtttggtaggtgagttaaccacgacgtgtcgccag | SEQ ID NO: 98 |
| F410 | cgtcgtggttaactcacctaccaaacaatgcccc | SEQ ID NO: 99 |
| R410 | cttttttgtcgtgtcatggtatatctccttttacccgcgacgcgcttttac | SEQ ID NO: 100 |

Example 5: Optimization of Fermentation in 5-L Fermentation Tank

Figure 2:
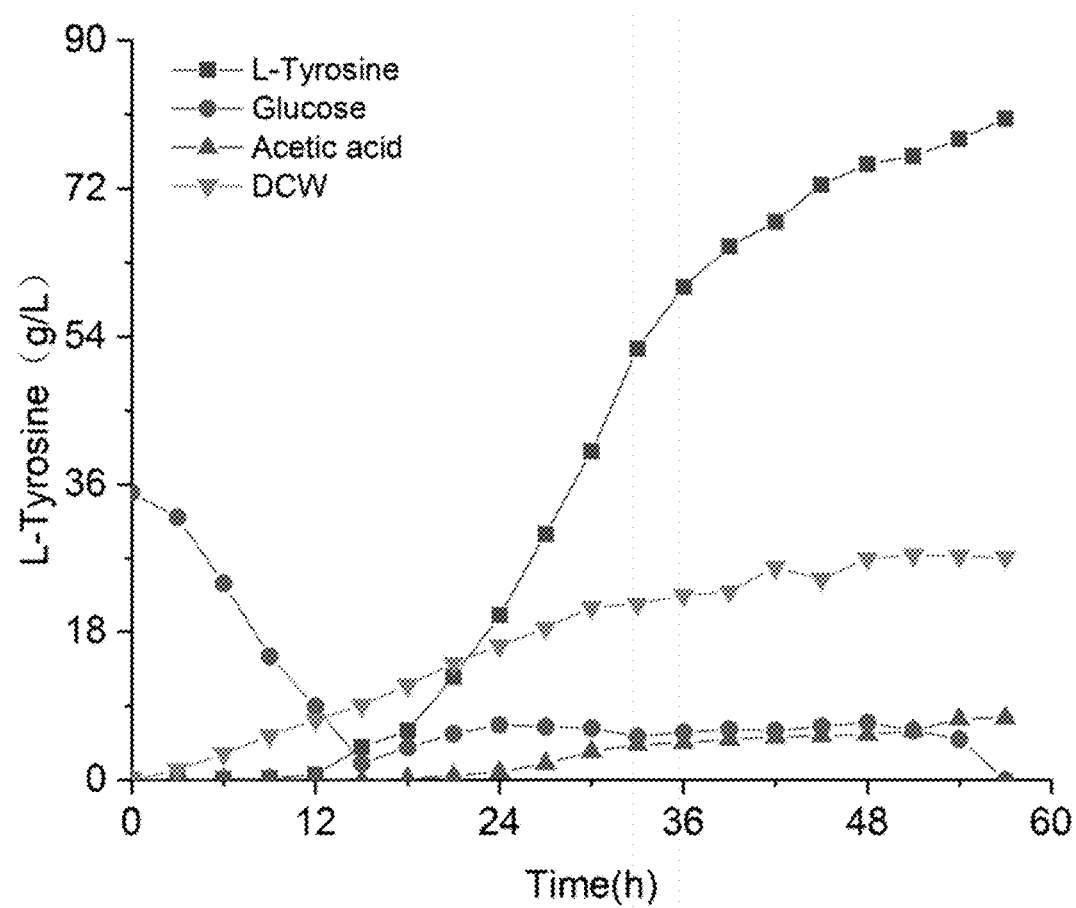
FIG. 2 is a diagram showing yield of L-tyrosine obtained by feed-batch fermentation of E. coli in a 5 L fermentation tank.

The engineered strain HGH constructed in Example 4 was inoculated into 50 mL of a seed culture medium and cultured at 220 rpm at 37° C. for 12 h to obtain a primary seed liquid, the primary seed liquid was inoculated into 50 mL of a secondary seed liquid at an inoculation amount of 2% (v/v), and then, the secondary seed liquid was inoculated into 2.5 L of a fermentation culture medium containing kanamycin with a final concentration of 50 μg/mL at an inoculation amount of 2% (v/v). With the initial rotation speed controlled at 300 rpm, the seed liquid was cultured at 33° C. for 12 h until the OD$_{600}$ value was 20-23, heated to 38° C. and continuously cultured for 48-55 h to obtain a fermentation liquid. In a whole fermentation process, the pH value was controlled at 6.4-6.6 by fed-batch 50% ammonia water; when the dissolved oxygen (DO) value was decreased to 20%, the rotation speed or the ventilation capacity was gradually increased to maintain the DO value at 20% or above; and when the glucose in a culture medium was depleted, a feeding procedure was started, and 750 g/L glucose was added to perform fed-batch fermentation, where the concentration of glucose was maintained at about 5-8 g/L. After completion of fermentation, the content of tyrosine was determined. Finally, as shown in FIG. 2, when the engineered strain HGH was subjected to fed-batch fermentation in a 5 L fermentation tank for 55 h, the accumulation content of tyrosine was 80.5 g/L, and the production intensity was 1.46 g/L/h.

Although the present disclosure has been disclosed as above through the preferred examples, the examples are not intended to limit the present disclosure. For any person familiar with the art, various changes and modifications can be made without departing from the spirit and scope of the present disclosure. Therefore, the protection scope of the present disclosure should be as defined in the claims.

What is claimed is:

1. A recombinant Escherichia coli for synthesis of L-tyrosine,
wherein the recombinant E. coli possesses a genome in which several first genes are knocked out, and comprises several added second genes that are expressed or overexpressed,
wherein the first genes knocked out consist of:
pheA encoding a fusion of chorismate mutase/prephenate dehydratase,
trpE encoding an anthranilate synthetase subunit TrpE,
tyrR encoding a DNA binding transcription double regulator TyrR,
poxB encoding pyruvate oxidase,
aroP encoding permease of an aromatic amino acid transporter AroP, and
tyrP encoding a tyrosine and H (+) symporter,
wherein the second genes added consist of:
aroG$^{fbr}$ encoding 3-deoxy-D-arabino-heptulosonate-7-phosphate synthase,
tyrA$^{fbr}$ encoding chorismate mutase and prephenate dehydrogenase,
fpk encoding phosphoketolase, and
yddG encoding an amino acid exportin YddG; and
wherein:
the pheA gene has the nucleotide sequence set forth in SEQ ID NO:1,
the trpE gene has the nucleotide sequence set forth in SEQ ID NO:2,
the aroG$^{fbr}$ gene has the nucleotide sequence set forth in SEQ ID NO:3,
the tyrA$^{fbr}$ gene has the nucleotide sequence set forth in SEQ ID NO:4,
the tyrR gene has the nucleotide sequence set forth in SEQ ID NO:5,
the fpk gene has the nucleotide sequence set forth in SEQ ID NO:8,
the poxB gene has the nucleotide sequence set forth in SEQ ID NO:9,
the aroP gene has the nucleotide sequence set forth in SEQ ID NO:10,
the tyrP gene has the nucleotide sequence set forth in SEQ ID NO:11, and
the yddG gene has the nucleotide sequence set forth in SEQ ID NO: 12;
wherein the recombinant E. coli genome additionally comprises integrated therein two genes consisting of:
ppsA expressing phosphoenolpyruvate synthetase, and
tktA encoding transketolase 1; and
wherein the ppsA gene has the nucleotide sequence set forth in SEQ ID NO:6,
wherein the tktA gene has the nucleotide sequence set forth in SEQ ID NO:7;
wherein the ppsA gene is integrated into the genome at a site ykgh-betA, and
wherein the tktA gene is integrated into the genome at a site dadx-cvra.

2. The recombinant E. coli according to claim 1, wherein the ppsA gene and the tktA gene are initially expressed by a promoter PJ$_{231119}$.

3. The recombinant E. coli according to claim 1, wherein the E. coli further comprises a heat induced expression vector pAP-B03.

4. The recombinant E. coli according to claim 1, wherein the E. coli is E. coli strain K12, BL21, DH5α, JM109, or WSH-Z06.

5. A method for producing L-tyrosine, which comprises:
fermenting the recombinant E. coli according to claim 1 under conditions conducive to fermentation of the recombinant E. coli.

6. The method according to claim 5, wherein said conditions conducive to fermentation comprises:
inoculating the recombinant E. coli into a fermentation system,
culturing the fermentation system at 32° C. to 34° C. for 3 hours to 12 hours, and
incubating with agitation at 200 rpm to 220 rpm and at a temperature of 36° C. to 40° C. for 48 hours to 60 hours.

7. The method according to claim 6, wherein the fermentation system comprises:
30 g/L to 40 g/L glucose,
3 g/L to 7 g/L (NH$_4$)$_2$SO$_4$,
1 g/L to 5 g/L KH$_2$PO$_4$,
1 g/L to 5 g/L MgSO$_4$·7H$_2$O,
1 g/L to 2 g/L sodium citrate,
0.5 g/L to 1.5 g/L NaCl,
0.05 g/L to 0.1 g/L vitamin B$_1$,
0.1 g/L to 0.12 g/L FeSO$_4$·7H$_2$O,
1 g/L to 3 g/L yeast powder,
2 g/L to 6 g/L peptone, and
1 ml/L to 2 ml/L trace element nutrient solution.

8. The recombinant E. coli according to claim 1, wherein the E. coli is E. coli strain WSH-Z06.

9. The recombinant E. coli according to claim 1, wherein the E. coli is produced by a process of:
mutating sequentially the genome by transforming the recombinant E. coli with recombinant vectors pCas9, pTarget-pheA, pTarget-TrpE, pAP-aroG$^{fbr}$-tyrA$^{fbr}$-ppsA-tktA, pTarget-tyrR, pTarget-dadx-cvra, pTarget-ykgh-betA, pAP-aroG$^{fbr}$-tyrA$^{fbr}$-fpk, pTarget-poxB, pTarget-aroP, and pTarget-tyrP, and
wherein the E. coli is E. coli strain WSH-Z06.

10. The recombinant E. coli according to claim 9, wherein said recombinant vectors are constructed by hybridization of primers having nucleotide sequences identical to those of SEQ ID NOS:13-100.

* * * * *

SEQUENCE LISTING

```
Sequence total quantity: 101
SEQ ID NO: 1              moltype = DNA   length = 1161
FEATURE                   Location/Qualifiers
source                    1..1161
                          mol_type = other DNA
                          organism = Escherichia coli
SEQUENCE: 1
atgacatcgg aaaacccgtt actggcgctg cgagagaaaa tcagcgcgct ggatgaaaaa   60
ttattagcgt tactggcaga acggcgcgaa ctggccgtcg aggtgggaaa agccaaactg  120
ctctcgcatc gcccggtacg tgatattgat cgtgaacgcg atttgctgga agattaatt   180
acgctcggta aagcgcacca tctggacgcc cattacatta ctcgcctgtt ccagctcatc  240
attgaagatt ccgtattaac tcagcaggct ttgctccaac aacatctcaa taaaattaat  300
ccgcactcag cacgcatcgc tttttctcgg cccaaaggtt cttattccca tcttgcggcg  360
cgccagtatg ctgcccgtca ctttgagcaa ttcattgaaa gtggctgcgc caaatttgcc  420
gatattttta atcaggtgga aaccggccag gccgactatc ccgtcgtacc gattgaaaat  480
accagctccg gtgccataaa cgacgtttac gatctgctgc aacataccag cttgtcgatt  540
gttggcgaga tgacgttaac tatcgaccat tgtttgttgg tctccggcac tactgattta  600
tccaccatca atacggtcta cagccatccg cagccattcc agcaatgcag caaattcctt  660
aatcgttatc cgcactggaa gattaatat accgaaagta cgtctgcggc aatgaaaaag  720
gttgcacagg caaaatcacc gcatgttgct gcgttgggaa gcgaagctgg cggcactttt  780
tacggtttgc aggtactgga gcgtattgaa gcaaatcagc gacaaaactt cacccgattt  840
gtggtgttgg cgcgtaaagc cattaacgtg tctgatcagg ttccggcgaa aaccacgttg  900
ttaatggcga ccgggcaaca agccggttgc gctggttgaa cgttgctggt actgcgaac   960
cacaatctga ttatgacccg tctggaatca cgcccgattc acggtaatcc atggaaagag 1020
atgttctatc tggatattca ggccaatctt gaatcagcgg aaatgcaaaa agcattgaaa 1080
gagttagggg aaatcacccg ttcaatgaag gtattgggct gttacccaag tgagaacgta 1140
gtgcctgttg atccaacctg a                                           1161

SEQ ID NO: 2              moltype = DNA   length = 1563
FEATURE                   Location/Qualifiers
source                    1..1563
                          mol_type = other DNA
                          organism = Escherichia coli
SEQUENCE: 2
tcagaaagtc tcctgtgcat gatgcgcggt ggcaatagcg cgcagtacag cgcgggcttt   60
gttacgggtt tcgtcggctt ccgactgcgg aacagaatca aggactacac cagcacccgc  120
ttgcacggtg gcgataccgt tttccaccag cgccgagcgg atcacaatgc aggtgtcgag  180
atcgccatgc gcggtgaaat aacctaccgc gccgccgtag ctgccgcggc gacgaccttc  240
cgcctcggca attaactgca tagcgcgtac tttcggcgca ccgcttaacg tcccatatt   300
catacaggcg cgataagcgt gcagggcgtc aagatcgtca gcagttcgc cgactacgcg   360
agagacgagg tgcatcacat aggaataacg gtcaactttg gtgagatcgg cgacgtagcg  420
gctgccgggg gtgcaaatgc gtgccagatc attacgggcg agatcaacca gcatcagatg  480
ttcagacagc tctttatgat cggtacgcat ttccagttca atacggctgt cgagatctct  540
gtccagtgaa ccatcggcgc gacgaccgcg tgggcgtgtt ccggcaatcg ggtagatctc  600
aatctggcgg ctggtggcat catacttgag cgagctttcc ggcgacgcgc caaatagggt  660
gaaatcatta tcctgcataa aaaacatgta cgggctggga ttactctttt tcagcacgta  720
ataggccgcc agcggtgacg ggcagggcag agagaaacgg cgagatggca ccacctggaa  780
aatttctcca gcgcgaatcg cttttttgcaa caaacgcact ccgccaccga actcttcatc  840
gctctgatta cattcacaac gcatatgcgg cacggaaacc actggcagcg cggcgcggc   900
ttcggtcagt tgctgacgta gttcgttcag gcgagcagtg agacgttgtt tttcttcttc   960
attcggagca acaggctggg cctgaatacg ggtgcttttt ttctgatggt caatcaccat  1020
cagcgtttca gcgagataaa aacagaaatc agggcagtta ttttccgctg acagttgcgg  1080
taaatcttca aatcccgcca caaggtcata agagaacagg ccgccgaaga acatgcgttg  1140
tcgttcttcc ttcggtacat tcaacagatt ctgcaataaa cggaaagcgt caaaaaccga  1200
aagggagcat aagcgggcgt cttcatccag cagtggactg acaggggga agcgcagcac   1260
acggcagttt ggtgattgtt cactttccac acccgcaggc agggcgttat ccagtagtgc  1320
caggagggct tcgccgttgc cggaaagtgc ctggattgtg acagtgtcac ctaaagctgt  1380
aatgcgcagc gcactgtcta ccagcagcag gctttttaaa tcatctttgc tgtcgatatc  1440
tgcggattcc agcagcagcg ttgccggacg atccccacac aactggtgaa aaagcggtt   1500
gggattgtcg cgataagcgc cttcgcaggt tagcagttcg agagtcggtt tttgtgtttg  1560
cat                                                               1563

SEQ ID NO: 3              moltype = DNA   length = 1053
FEATURE                   Location/Qualifiers
source                    1..1053
                          mol_type = other DNA
                          organism = Escherichia coli
SEQUENCE: 3
atgaattatc agaacgacga tttacgcatc aaagaaatca aagagttact tcctcctgtc   60
gcattgctgg aaaaattccc cgctactgaa aatgccgcga atacggttgc ccatgcccga  120
aaagcgatcc ataagatcct gaaaggtaat gatgatcgcc tgttggttgt gattggccca  180
tgctcaattc atgatcctgt cgcggcaaaa gagtatgcca ctcgcttgct ggcgctgcgt  240
gaagagcga aagatgagct ggaaatcgta atgcgtgtct attttgaaaa gccgcgtacc  300
acgtgggct ggaaagggct gattaacgat ccgcatatgg ataatagctt ccagatcaac  360
gacggtctgc gtagcccg taaattgctg cttgatatta cgacagcgg tctgccagcg  420
gcaggtgagt ttctcgatat gatcaccca caatatctcg ctgacctgat gagctgggc   480
gcaattggcc cacgtaccac cgaatcgcag gtgcaccgcg aactggcatc agggcttct   540
tgtccggtcg gcttcaaaaa tggcaccgac ggtacgatta agtggctat cgatgccatt  600
```

```
aatgccgccg gtgcgccgca ctgcttcctg tccgtaacga aatggggca ttcggcgatt    660
gtgaatacca gcggtaacgg cgattggcat atcattctgc gcggcggtaa agagcctaac    720
tacagcgcga agcacgttgc tgaagtgaaa aagggctga acaaagcagg cctgccagca    780
caggtgatga tcgatttcag ccatgctaac tcgtccaaac aattcaaaaa gcagatggat    840
gtttgtgctg acgtttgcca gcagattgcc ggtggcgaaa aggccattat tggcgtgatg    900
gtggaaagcc atctggtgga aggcaatcag agcctcgaga gcggggagcc gctggcctac    960
ggtaagagca tcaccgatgc ctgcatcggc tgggaagata ccgatgctct gttacgtcaa    1020
ctggcgaatg cagtaaaagc gcgtcgcggg taa                                 1053

SEQ ID NO: 4          moltype = DNA   length = 1122
FEATURE               Location/Qualifiers
source                1..1122
                      mol_type = other DNA
                      organism = Escherichia coli
SEQUENCE: 4
ttactggcga ttgtcattcg cctgacgcaa taacacgcgg cttcactct gaaaacgctg      60
tgcgtaatcg ccgaaccagt gctccacctt gcggaaactg tcaataaacg cctgcttatc    120
gccctgctcc agcaactcaa tcgcctcgcc gaaacgctta gtaacgtt tgattaacgc     180
cagattacgc tctgacgaca taatgatgtc ggcataaagc tgcggatcct gagcaaacag    240
tcgcccgacc atcgccagct caaggcggta aatcggcgaa gagagcgcca gaagttgctc    300
aagctgaaca ttttcttctg ccaggtgcag cccgtaagca aaagtagcaa agtggcgcag    360
tgcctgaata aacgccatat tctgatcgtg ctcgacggcg ctaatacgat gcagccgagc    420
gccccagacc tgaatttgct ccagaaacca ttggtatgct tccggtttac gtccatcaca    480
ccagaccaca acttgctttg ccaggctacc gctgtccgga ccgaacatcg ggtgtagccc    540
cagcaccgga ccatcatgcg ccaccagcat ggcctgtaat ggcccatttt tcactgatgc    600
cagatcgacc agaatacaat cttttcggtaa aggcggtaat ttgccaataa cttgctcagt    660
aacgtggatt ggcacactaa caatcaccat tccggcatcg gcaacaatat cagccgctcg    720
atcccagtca tgttgctcca gaatccgcac ctgataaccc gagagggtca gcatcttctc    780
gaacaggcgt cccatctgac cgccaccgcc gacgataacc accggacgca gtgacggaca    840
aagtgtttta aatcctttgt cgtttcact ggagtaagat tcacgcatca cccgacgcaa     900
aacatcctca atcagatctg gcggtacacc cagagcttcc gcctctgcac gacgcgaggc    960
caacatagat gcctcgcgct ccggaacata aataggcagt ccaaagcggc ttttcacctc    1020
gcccacttca gcaaccagtt ccagacgctt cgctaataaa ttcagcagcg ctttatcgac    1080
ttcatcaatt tgatcgcgta atgcggtcaa ttcagcaacc at                       1122

SEQ ID NO: 5          moltype = DNA   length = 1542
FEATURE               Location/Qualifiers
source                1..1542
                      mol_type = other DNA
                      organism = Escherichia coli
SEQUENCE: 5
atgcgtctgg aagtcttttg tgaagaccga ctcggtctga cccgcgaatt actcgatcta     60
ctcgtgctaa gaggcattga tttacgcggt attgagattg atcccattgg gcgaatctac    120
ctcaattttg ctgaactgga gtttgagagt ttcagcagtc tgatggccga aatacgccgt    180
attgcgggtg ttaccgatgt gcgtactgtc ccgtggatgc cttccgaacg tgagcatctg    240
gcgttgagcg cgttactgga ggcgttgcct gaacctgtgc tctctgtcga tatgaaaagc    300
aaagtggata tggcgaaccc ggcgagctgt cagcttttttg ggcaaaaatt ggatcgcctg    360
cgcaaccata ccgccgcaca attgattaac ggctttaatt ttttacgttg gctgaaaagc    420
gaaccgcaag attcgcataa cgagcatgtc gttattaatg ggcagaattt cctgatggag    480
attacgcctg tttatcttca ggatgaaaat gatcaacacg tcctgaccgg tgcggtggtg    540
atgttgcgat caacgattcg tatgggccgc cagttgcaaa atgtcgccgc ccaggacgtc    600
agcgccttca gtcaaattgt cgccgtcagc ccgaaaatga agcatgttgt cgaacaggcg    660
cagaaactgg cgatgctaag cgccgccgct ctgattacgg gtgacacagg tacaggtaaa    720
gatctctttg cctacgcctg ccatcaggca agccccagag cggcaaaacc ttacctggcg    780
ctgaactgtg cgtctatacc ggaagatgcg gtcgagagtg aactgtttgg tcatgctccg    840
gaagggaaga aaggattctt tgagcaggca aacggtggtt cggtgctgtt ggatgaaata    900
ggggaaatgt caccacggat gcaggcgaaa ttactgcgtt tccttaatga tggcacttc     960
cgtcgggttg gcgaagacca tgaggtgcat gtcgatgtgc gggtgatttg cgctacgcag    1020
aagaatctgg tcgaactggt gcaaaaaggc atgttccgtg aagatctcta ttatcgtctg    1080
aacgtgttga cgctcaatct gccgccgcta cgtgactgtc gcaggacat catgccgtta    1140
actgagctgt tcgtcgcccg ctttgccgac gagcagggcg tgccgcgtcc gaaactggcc    1200
gctgacctga atactgtact tacgcgttat gcgtggccgg gaaatgtgcg gcagttaaag    1260
aacgctatct atcgcgcact gacacaactg gacggttatg agctgcgtcc acaggatatt    1320
ttgttgccgg attatgacgc cgcaacggta gccgtgggta agatgcgat ggaaggttcg     1380
ctggacgaaa tcaccagccg ttttgaacgc tcggtattaa cccagctta tcgcaattat     1440
cccagcacgc gcaaactggc aaaacgtctc ggctttcac ataccgcgat tgccaataag     1500
ttgcgggaat atggtctgag tcagaagaag aacgaagagt aa                       1542

SEQ ID NO: 6          moltype = DNA   length = 2379
FEATURE               Location/Qualifiers
source                1..2379
                      mol_type = other DNA
                      organism = Escherichia coli
SEQUENCE: 6
ttatttcttc agttcagcca ggcttaacca ggtttgcacc acggtgtccg ggttcagaga     60
caggctatcg atcccctctt ccatcaacca tgcggcaaag tcttcgtggt cggacggacc    120
ctgaccgcaa atcccgacat atttgccctg tttcttcgcg gcacggatag ccatcgacag    180
cagtgctttc accgcatcgt tgcgctcatc gaacaattca gacaccacgc cggagtcacg    240
gtccagaccg agcgccagct gcgtcatatc gtttgagcca attgagaagc cgtcgaaata    300
```

```
ttcgaggaac tgctcggcca gcaaggcgtt ggacgggatt tcacacatca tgatgatttt   360
cagcccgttc tcgccacgtt tcagcccctg acgcgccagt tcttcaacca ccgctttcgc   420
ctgatctacg gtacgcacga acgggatcat gatctcaacg ttggtcagtc ccatgtcgtt   480
gcgcacacgt ttcactgctt cacactccag cgcgaaacag tcgcggaagc tgtcggaaac   540
ataggggccc gcgccacgga agccgagcat cgggttctct tcatctggct cgtaacgctc   600
accaccgacc aggttggcat attcgttcga tttaaaatca gagagacgga caatgacgcg   660
cttcggataa aacgcggcac ccagcgtcgc gatcccttca gtcagacgac caacgtaaaa   720
ttcacgcgga gaatcaaaac cttttcatcat ctcgcggatt tcgttttgca actgcggttc   780
ctgatcgtca aactcaagca gtgcgcgtgg gtggacgcca atcatacggt tgatgataaa   840
ttccagacgc gcaaggccca cgccttcgtt cggtaggcag gcgaagtcga aagcacggtc   900
cgggttaccg acgttcatca tcactttcaa cggcagatcc ggcatcgttt ctacgctgga   960
gcttttcacg ctaaattcca gcaactccgc atagacgtaa ccggtatcac cttcggcaca  1020
agaaacagtg acgttctcac cgtctttcat ccgttctgtt gcatctccac agcccactac  1080
cgccgaaatg cccagttcac gagcgatgat cgccgcgtga caggtacgac cgcacggtt   1140
ggtgacgatg gcagatgctt tcttcatgat cggttcccag tccgggtcgg tcatgtcagt  1200
aaccagcacg tcgccaggtt cgatgcgtt catttcgctg atgtcatgga tgactttcac  1260
cggacccgca ccgatgcgat gaccgatagc acggccttcg gcgataatct taccctgtga  1320
atgcagcgta taacgctcca tgacctgacc gcgtgagcgc acggttttccg gacgcgccta  1380
cacaatgaac agtttaccgg tgtggccatc tttcgcccac tcaatatcca tcgggcgacc  1440
gtagtgtttc tcaatttgta cggcctgttt tgccagttcc tgcacttctt cgttggtcag  1500
cgagaagatg tcacgctgtt cctgcggtac gtcttcgatt ttaacctgct tgccgtgctc  1560
ctgggtcggc gcgtaaacca tgcggatttt tttcgacccc atggtgcggc gcacgatagc  1620
cgggcgattc gccgccagtg tcggtttatg cacgtaaaac tcatccgggt taaccgcacc  1680
ctgcacgacc atctccaccaa ggccccatgc ggaagtgata aacaccacct ggtcaaagcc  1740
ggattcggta tcaatggaga acatcacgcc agatgatgcg aggtcagagc gcaccatccg  1800
ttgaacaccg gcggagagcg ccacaccacg gtgatcgtaa ccctggtgca cacgataaga  1860
gatggcgcga tcgttaaaca gagaagcaaa tacatgtttc actgccacga gaacggcgtc  1920
aaaaccctga acgttgagga aggtttcctg ctgaccggca aaagaagcgt ccggcatatc  1980
ttctgcggtg gcggaggagc gcaccgcaaa agaggcgttt tcgtcatcgg cggaaagctg  2040
tgcataggct tcgcggatgg cgttttccag ctcaggctgg aagggagtgt cgataatcca  2100
ctggcggatt tgcgcgcccg ctttcgcaag ctgagtaaca tcgtcaatat ccgttttatc  2160
cagcagttca taaatgcgct ggtttacgcc gctttggtcc agaaactggt taaacgcgtc  2220
ggcggttgtg gcgaaaccat tcggaacgga aacacccatt ccggaaagat tagtaatcat  2280
ttcacccagg gaggcatttt tgcccccaac cctgtctaca tcattcatgc cgagttggtt  2340
ataccaaagc accagcggtg acgagccatt gttggacat                        2379

SEQ ID NO: 7            moltype = DNA  length = 1992
FEATURE                 Location/Qualifiers
source                  1..1992
                        mol_type = other DNA
                        organism = Escherichia coli
SEQUENCE: 7
ttacagcagt tcttttgctt tcgcaacaac gttatcaaca gtgaagccga actcttcaaa    60
cagcagctct gccggagcag attcaccgaa ggtggtcata ccgacgatag caccgttcag   120
gccaacatac ttgtaccagt agtcagcaat accgcttct acagcaacgc gtgcagtaac   180
cgcttcgcc agtacggatt cacggtaagc agcatcctgc ttgtcaaatg cgtcggtaga   240
cggcatggac accacgcgcg cttttcacgcc ttcggcagtc agtttttcgt aggcagcaac   300
agccagttca acttctgaac cggtagcgat gaaaatcagt tccggctgac cggcgcagtc   360
tttcagcaca taaccaccgc gcgcgatgtt tgccagttgc tcttcagttc gttcctgctg   420
cgccaggttc tgacgggaga ggatcagtgc ggtcgggccg tcctgacgct caacaccgta   480
tttccacgcg accgcggatt caacctggtc acacggacgc catgtagaca tgttcggata   540
tacgcgcaga gaagcgacct gctcaaccgg ctggtgagtc gggccgtctt cgcccagacc   600
gatggagtcg tgggtgtaaa ccatcacctg acgctgtttc atcagcgcag ccatacgtac   660
ggcgttacgt gcgtattcca cgaacatcag gaaggtggag gtgtacggca ggaagccacc   720
gtgcagggag ataccgttag caatgcgggt cataccgaac tcgcgaacac cgtagtggat   780
gtagttaccc gcagcatctt cgttgattgc tttagaacca gaccacaggg tcaggttaga   840
cggcgccagg tcagcagaac cgccgaggaa ttccggcaac agcggaccga acgcttcgat   900
agcattctga gacgctttac ggctggcgat tttgccgga ttagcctgca gtttagcgat   960
gaactcttttc gctttagcgt cgaagtcaga cggcatttc cctttcatac ggcgggtaaa  1020
ttcagcggct tcctgcggat aagctttcgc gtaagcagcg aatttctcgt tccatgcgga  1080
ttctttcgcc tggcctgctt ctttcgcatc ccactgagca tagatttcag acgggattc   1140
gaacggcgca tatttccagc ccagttgttc gcgggtcagg gcaatttcag cgtcgcccag  1200
cggcgcaccg tgggagtcgt gggtaccggc tttgttcggg gaaccgaaac cgatgatggt  1260
tttgcacatc agcagggaag gttttgtcagt cactgccgca gcttcttcta ctgcgcgttt  1320
gatagatgcc gcgtcatgac cgtcgatgtc gcgaataacg tgccagccgt aagcttcgaa  1380
acgcattgcg gtgtcgtcgg tgaaccagcc ttcaacgtga ccatcgatag aaataccgtt  1440
gtcatcgtag aatgcaatca gtttacccag cttcagcgta cccgccagag agcaaacttc  1500
gtgggagatg ccttccatca tgcagccgtc gcccatgaag gcgtaggtgt agtggtcgac  1560
aatgtcggcc cccggacggt taaactgcgc cgccagcgtt ttttctgcaa tcgccatacc  1620
gactgcgttg gcaatacct gacccagcgg accggtggtg gtttccacac cagcggtgta  1680
acccacttcc gggtgacccg gagtttttaga gtgcagctga cggaagtttt tcagttcttc  1740
catcggcaga tcgtaaccgg tgaggtgcag caggctgtag atcagcatgg agccgtggcc  1800
gttggacagc acgaagcgt cacggtcagc ccaggacgga ttctgcgggt tgtgtttcag  1860
gaaatcacgc cacaggactt cggcaatgtc agccataccc ataggggcac ccgggtgacc  1920
ggatttggct ttctgtactg cgtccatgct cagcgcacga atagcattgg caagctcttt  1980
acgtgaggac at                                                     1992

SEQ ID NO: 8            moltype = DNA  length = 2478
FEATURE                 Location/Qualifiers
```

| source | 1..2478 |
| --- | --- |
| | mol_type = other DNA |
| | organism = Bifidobacterium adolescentis |

SEQUENCE: 8

```
atgactaacc ctgtaatcgg tactccttgg caaaagttgg atagaccagt tcagaagaa    60
gcaatcgaag gtatggataa atattggaga gttaccaact atatgtccat aggtcaaatc   120
tacttgagaa gtaacccatt gatgaaggaa cctttacta gagatgacgt taagcataga    180
ttagtcggtc actggggtac tacaccaggt ttgaacttct tgttggccca tatcaacaga   240
ttgatcgctg atcaccaaca aaacaccgtt tttataatgg gtccaggtca tggtggtcca   300
gctggtactt cccaaagtta tgttgacggt acttacactg aatactaccc aaacataaca   360
aaagatgaag ctggtttgca aaagtttttc agacaattct cctatccagg tggtatccct   420
agtcatttg caccagaaac ccctggttca attcacgaag tggtgaatt gggttatgct     480
ttatctcatg cttacggtgc agtaatgaat aacccatcat tgtttgttcc ttgtattata   540
ggtgacggtg aagccgaaac aggtccatta gctaccggtt ggcaatctaa caaattgct    600
aatccaagaa ctgatggtat cgtattgcct atcttgcatt gaacggtta caagattgca    660
aatccaacaa tcttggccag aatatctgat gaagaattac atgactttt ccgtggtatg    720
ggttatcacc cttacgaatt tgttgccggt tcgataatg aagaccacat gtctatccac   780
agaagattcg ctgaattgtt cgaaactatc ttcgatgaaa tttgtgacat aaaagctgct   840
gctcaaaccg atgacatgac tagaccattc taccctatgt tgatttttag aactccaaag   900
ggttggacat gccctaagtt catcgatggt aaaaagacag aaggttcctg gagagcacat   960
caagttccat tagctagtgc aagagatacc gaagaacact ttgaagtctt gaaaggttgg  1020
atggaatctt acaagcctga agaattattc aatgcagatg gttcaattaa agatgacgtt  1080
acagccttta tgccaaaggg tgaattgaga ataggtgcca atcctaacgc taatggtggt  1140
gttatcagag aagatttgaa attgccagaa ttagaccaat gtgaagtaac tggtgttaag  1200
gaatacggtc atggttgggg tcaagttgaa gcccctagag ctttgggtgc atattgtaga  1260
gatatcatta aaataaccc agactccttt agaaatattgc gtcctgatga aacagctagt  1320
aacagattga acgcaactta tgaagtaacc gataagcaat gggacaatgg ttacttgtct  1380
ggtttagttg atgaacacat ggcagtcact ggtcaagtaa cagaacaatt atcagaacac  1440
caatgcgaag gtttcttgga agcatatttg ttaacaggta gacatggtat ttggtcttca  1500
tacgaatctt ttgtacatgt tatcgattca atgttgaacc aacacgccaa agttagaa    1560
gctactgtta gagaaatacc ttggagaaag cctatctcca gtgttaactt gttagtctct  1620
tcacatgtat ggagacaaga tcataatggt ttttctcacc aagacccagg tgtcacatca  1680
tgttgatta ataagaccct caataacgat cacgttacca acatctattt tgccactgac   1740
gctaacatgt tgttggctat ctctgaaaag tgcttcaagt caactaacaa aatcaatgca  1800
atattcgccg gtaaacaacc agcacctaca tgggttacct tggatgaagc cagagctgaa  1860
ttagaagctg tgctgctga atggaaatgg gcttctaatg cagaaaataa cgatgaagtt   1920
caagttgtct tggcatccgc cggtgacgtc ccaacacaag aattgatggc cgctagtgat  1980
gctttgaaca aaatgggtat taagtttaaa gtagttaacg tcgtagattt gttgaagtta  2040
caatcaagag aaaacaacga tgaagcattg actgacgaag agtttactga attgttttact 2100
gctgataaac cagtattgtt tgcatatcat tcctacgccc aagatgttag aggtttgatc  2160
tatgatagac caaccatga caatttccac gttgtcggtt acaaagaaca aggttcaacc  2220
actacacctt ttgatatggt cagagtaaat gatatgacca gatatgcatt gcaagcagcc  2280
gctttgaagt taattgatgc agacaaatac gccgataaga tcgacgaatt aaacgcttc   2340
agaaagaaag catttcaatt cgcagtcgat aatggttatg acattccaga gtttactgat  2400
tgggtatacc ctgatgttaa ggttgatgaa acacaaatgt tgtctgctac tgctgctact  2460
gctggtgaca atgaataa                                                2478
```

| SEQ ID NO: 9 | moltype = DNA length = 1719 |
| --- | --- |
| FEATURE | Location/Qualifiers |
| source | 1..1719 |
| | mol_type = other DNA |
| | organism = Escherichia coli |

SEQUENCE: 9

```
ttaccttagc cagtttgttt tcgccagttc gatcacttca tcaccgcgtc cgctgatgat    60
tgcgcgcagc atatacaggc tgaaaccttt ggcctgttcg agtttgatct gcggtggaat   120
ggctaactct tctttggcga ccaccacatc caccaacacc ggaccgtcga tggagaaggc   180
gcgttgcagg gcttcatcaa cttcagacgc ttttctaca cggataccccg taatgccgca    240
cgcttcggca atgcgggcaa agtttgtgtc gtgtagttcg gtgccgtcag tcaaatagcc   300
accagctttc atctccatcg ccacaaagcc cagcacgctg ttgttaaaga cgacaatttt   360
cactggcagt ttcatctgca ctactgagag gaaatcgccc atcaacatgc taaaaccgcc   420
atcgccgcac atggcgacca cctgacgttc tggctctgtc gcctgcgcac ccagcgcctg   480
cggcatggcg ttagccatcg aaccgtggtt aaacgaacct aacaggcgac gcttgccgtt   540
catttttaga taacgtgccg cccacaccgt tggcgtacca acgtcacagg tgaaaatagc   600
gtcatcggcg gcaaaatgac taatttgctg cgccagatat tgcgggtgaa tgcgcttttc  660
gctcggttta gctaaatcgt ccagcccttt gcgggcgtcg cggtaatctt ccagcgcttt  720
atccagaaac ttgcgatcgg cttttttctc caccaatgga agcaatgcac gcagagtcga   780
cttgatatcg ccgaccagtg ccatatccac cttgctgtga cgccgatgc tggctggtt    840
gatatcaatc tgaatgattt tggcatcggt cgggtagaag gcgcggtagg gaaattgcgt   900
gccgagtagc actaacgtgt gcgcgttcat catggtatgg aaacctgacg agaagccgat   960
taacccggtc attccaacat catacggatt atcgtattcg acatgttctt taccgcgcag  1020
ggcatgaaca ataggcgctt taattttccc ggcaaactca actaactctt tatgcgcccc  1080
cgcgcagccc ctgccacaca tcagggcgat attgctggaa taacgcagca gttgcgccag  1140
tttgcgtaac tcttcttctt ccggcgtcac gactggtggt ggcgcatgat accagtgcat  1200
ggttgcccct tctggcgcag gttttaacgc cacgtgcgtc ggtaacacga caaccgaaac  1260
gccacggtta agcaccgctt tgccgcatgg caatccgcagt acttgtggga tctgctccgg  1320
gctgaaaacc agctcgcaat agtgactaca ttccgcgaat agctcttgtg ggtgggttc   1380
ctggaaatag ccgctgccaa tttgctggaa gggaatatga gcggcaatcg ccagtaccgg  1440
aacgtgattg cggtggcaat cgaacaggcc gttgattaag tgcaggttgc cggggccgca  1500
cgatccggcg cagaccgcca gttctccgct aagttgtgct tcagcgccag cggcaaaggc  1560
```

```
cgccacttct tcgtggcggg tggacatcca ctcgatgcgt cccatgcgat taagactgtc   1620
actaagaccg ttcagagagt cgcctgtgac tccccagatg cgtttcaccc ctgccgattc   1680
gagtgttttg gcgatataag ctgcaaccgt ttgtttcat                          1719

SEQ ID NO: 10           moltype = DNA   length = 1374
FEATURE                 Location/Qualifiers
source                  1..1374
                        mol_type = other DNA
                        organism = Escherichia coli
SEQUENCE: 10
ttaatgcgct tttacggctt tggcggtttt ctctttaaac agatagccga tacctaacac     60
gatcagccat accgggatca ggtataccga aatcgccatt cctggggtca tcagcataat    120
caccagtacc gccgccataa acagcaggca gatccagtta cccagcggat aaagcagagc    180
agggaagcga gttaccacgc cttgttcctg cttggcgcga gggaatttca tatgcgccag    240
gctaatcatc gcccagttga ttaccagtgc agataccacc agcgccatta acagtccgaa    300
agcggactct ggggcaaggt agttaatcag tacgcacaac gccgttacca gtgcagacac    360
cagaatggta tttactggta caccacgttt atcgacagac gccagcgctt ttggcgcatt    420
accctgttgt gccagaccaa acagcatacg gctgttgcaa tatacgcagc tgttgtacac    480
ggagagcgcc gcagtcagta ccacgatgtt cagcgcattc gccacaaagg tatcgcctaa    540
ctcgtggaag atcagcacaa acggactggt atcggcggta acgcgggtcc acggcatcag    600
tgagagcaga acggctaacg aaccaatata gaaaatcagg atgcggtaga taacctggtt    660
agttgctttc ggtatacttt gctccgggtt atcagctgtc gctgcggtga ttcccaccag    720
ttccagacca ccgaacgaga acatgataat cgccatcatc atcaccagcc cggtgaagcc    780
gtgcggcagg aaaccaccct gatcccacag gttgctaacg gtcgcctgcg ggccgccgtt    840
gccactgaat agcagccagc cgccgaagat gatcatcgct accaccgcga taactttgat    900
aatggcaaac cagaactcca tctcgccaaa cactttaacg ttggtcaggt tgatgcgtt     960
aatcaccaca aagaatacgg cggcagaaac ccaggtgggg atttccggat accagaactg   1020
aatgtattta cccacggcag tcagctcagc catggcaact aaaacgtaca gtacccagta   1080
gttccagcca gaggcgaaac cggcaaaact gccccagtat ttataagcaa agtggctaaa   1140
ggagcctgcg acaggttctt cgaccaccat ttcacccagc tgcgcatga tcagaaaggc   1200
gataaaacca gcaatggcgt aacccaggat aatcccctggc cctgcggact gtattacgga   1260
ggcgctaccc aggaataacc cggtccctat cgcgccaccc agcgcgataa gctgaatatg   1320
gcggttttta aggccgcgct ttagctgctc gccgtgctgt tgaccttcca tcat         1374

SEQ ID NO: 11           moltype = DNA   length = 1212
FEATURE                 Location/Qualifiers
source                  1..1212
                        mol_type = other DNA
                        organism = Escherichia coli
SEQUENCE: 11
gtgaaaaaca gaaccctggg aagtgttttt atcgtggcgg gaaccacaat tggcgcaggc     60
atgctggcaa tgccgctggc tgcggccggt gttggtttta gcgttacgtt aatcttgttg    120
attgggcttt gggcgttgat gtgctacacg cgctattacc tgctggaggt gtaccagcat    180
gttccggcag ataccggtct gggcacgctg gcaaaacgct atctgggacg ctacggtcaa    240
tggctgacgg gcttcagtat gatgttctta atgtatgctc tgactgcggc atacatcagc    300
ggtgccggtg aattgttggc ctccagcatc agcgactgga caggtatttc tatgtcggca    360
accgctggcg tgctgtttgt cacttttgtt gccggtgggt tggtttgtgt cggaacttca    420
ctggtcgatt tatttaaccg ttttctgttc agcgccaaga ttattttttct ggtggtaatg    480
ctggtactac tgctgccgca tattcacaaa gtgaatcttt taaccctgcc gttgcaacag    540
gggctggctc tgtctgcaat cccggtgatt tttacgtcgt ttggttttca cggtagcgtg    600
ccgagtattg tcagctatat ggatggcaac attcgtaagc tacgctgggt gtttatatc     660
ggtagtgcga tcccctggt ggcatatatt ttctggcagg tggcgacgct tggcagcatt    720
gattcaacaa cctttatggg attgctggct aatcatgctg gattaaacgg gctgttacag    780
gcgttacgcg aaatggtggc ctctccgcat gttgagctgg cagtgcattt atttgctgat    840
ttagcccctcg ccacgtcatt tctcggcgtt cgttaggct tatttgatta tctgctgat    900
ttatttcagc gttcaaatac cgttggtgga cggttgcaaa ctggtgcaat tacgtttctg    960
ccgccgttgg cgtttgcact gttttatcca cgaggatttg tgatggcgct gggttacgcc   1020
ggtgtggcgc tggcggtact ggcattgatt atcccttcgc tgttgacctg gcaaagcaga   1080
aagcacaatc ctcaggcggg ttaccgggtc aaaggtggtc gtccggcgct ggtggtggtg   1140
tttctctgtg gtattgctgt gattggcgtg caattttga ttgcggcagg ttgttaccaa   1200
gaagtggggt ga                                                       1212

SEQ ID NO: 12           moltype = DNA   length = 882
FEATURE                 Location/Qualifiers
source                  1..882
                        mol_type = other DNA
                        organism = Escherichia coli
SEQUENCE: 12
ttaaccacga cgtgtcgcca gccagcagag caggggaaccg ccgcagacca tcagcgcgcc     60
ttgccagaac gagaacgaca gcggggcgct gagcagcacg gctgcaagcg ctgaggaaag    120
tacaggcgta aaatacgaac ctaccgccat aatggtgaca ttgccatgca atataccgac    180
attccatgca gcataagcaa atcctaaggt aaatgccgca gagatgagtt taatcatgac    240
gggcgtgcta aatatcattt ctggttgtgg cgtaagaaaa tagtaaaccc acagacttgc    300
tcccgttagc aggacaaaaa cggtaattcc attaaatccg cgtgcgtatt tattcgttac    360
tgtgcaatag gctgcccaga taaacgcacc aatgaacgcc aggaaataac tcaatgggct    420
ggtggtgata ttattgatga tttcatcata atgtaaccca ttgtcaccgc ctaacaccca    480
acagacgccg acgagggcta ataataatcc aggtacaatc aaccagttgg ttttctgacc    540
attaaacaga atggcaaaga gaattgtcag gctgggccac agatagttca ccatacccac    600
ttcaatcgcc tgatgatggg tcgccgcata ccctaaggaa agcgccagac agatttcata    660
```

```
gctgacgaat aacagactcc cggcgagtaa atagcctttc ggatttgcc gaatacgcgg    720
aaatccaacc gtgaagatta acagcagccc gcttaatgaa tagatagcag ctgcgccgcc    780
gaccgggccg agcccctcac tgacaccgcg aatcaatcct accatcgtgc tccacaggac    840
gatcgctatc agcccatga gcgttgcttt ttgtcgtgtc at                        882

SEQ ID NO: 13           moltype = DNA   length = 24
FEATURE                 Location/Qualifiers
source                  1..24
                        mol_type = other DNA
                        organism = synthetic construct
SEQUENCE: 13
cgtctcgcca aactggaaaa atgg                                            24

SEQ ID NO: 14           moltype = DNA   length = 30
FEATURE                 Location/Qualifiers
source                  1..30
                        mol_type = other DNA
                        organism = synthetic construct
SEQUENCE: 14
cttttcaccc cgatttggga ggccttattg                                      30

SEQ ID NO: 15           moltype = DNA   length = 44
FEATURE                 Location/Qualifiers
source                  1..44
                        mol_type = other DNA
                        organism = synthetic construct
SEQUENCE: 15
ctcccaaatc ggggtgaaaa ggtgccggat gatgtgaatc atcc                      44

SEQ ID NO: 16           moltype = DNA   length = 29
FEATURE                 Location/Qualifiers
source                  1..29
                        mol_type = other DNA
                        organism = synthetic construct
SEQUENCE: 16
caatggtttc tggagcaaat tcaggtctg                                       29

SEQ ID NO: 17           moltype = DNA   length = 58
FEATURE                 Location/Qualifiers
source                  1..58
                        mol_type = other DNA
                        organism = synthetic construct
SEQUENCE: 17
atataccgaa agtacgtctg gttttagagc tagaaatagc aagttaaaat aaggctag       58

SEQ ID NO: 18           moltype = DNA   length = 51
FEATURE                 Location/Qualifiers
source                  1..51
                        mol_type = other DNA
                        organism = synthetic construct
SEQUENCE: 18
cagacgtact ttcggtatat actagtatta tacctaggac tgagctagct g              51

SEQ ID NO: 19           moltype = DNA   length = 27
FEATURE                 Location/Qualifiers
source                  1..27
                        mol_type = other DNA
                        organism = synthetic construct
SEQUENCE: 19
ccagcaaaca aatggaaatt actccgg                                         27

SEQ ID NO: 20           moltype = DNA   length = 24
FEATURE                 Location/Qualifiers
source                  1..24
                        mol_type = other DNA
                        organism = synthetic construct
SEQUENCE: 20
gtctggtgtg atggacgtaa accg                                            24

SEQ ID NO: 21           moltype = DNA   length = 24
FEATURE                 Location/Qualifiers
source                  1..24
                        mol_type = other DNA
                        organism = synthetic construct
SEQUENCE: 21
ccaggcgttc aattaaggtt tgcg                                            24

SEQ ID NO: 22           moltype = DNA   length = 35
FEATURE                 Location/Qualifiers
```

```
source                      1..35
                            mol_type = other DNA
                            organism = synthetic construct
SEQUENCE: 22
gtttttatct cgccgaactg cgtcacgatc ttgac                              35

SEQ ID NO: 23               moltype = DNA   length = 38
FEATURE                     Location/Qualifiers
source                      1..38
                            mol_type = other DNA
                            organism = synthetic construct
SEQUENCE: 23
gacgcagttc ggcgagataa aaacagaaat cagggcag                           38

SEQ ID NO: 24               moltype = DNA   length = 23
FEATURE                     Location/Qualifiers
source                      1..23
                            mol_type = other DNA
                            organism = synthetic construct
SEQUENCE: 24
cgactctcga actgctaacc tgc                                           23

SEQ ID NO: 25               moltype = DNA   length = 54
FEATURE                     Location/Qualifiers
source                      1..54
                            mol_type = other DNA
                            organism = synthetic construct
SEQUENCE: 25
attgccggaa cacgcccacg gttttagagc tagaaatagc aagttaaaat aagg         54

SEQ ID NO: 26               moltype = DNA   length = 51
FEATURE                     Location/Qualifiers
source                      1..51
                            mol_type = other DNA
                            organism = synthetic construct
SEQUENCE: 26
cgtgggcgtg ttccggcaat actagtatta tacctaggac tgagctagct g            51

SEQ ID NO: 27               moltype = DNA   length = 21
FEATURE                     Location/Qualifiers
source                      1..21
                            mol_type = other DNA
                            organism = synthetic construct
SEQUENCE: 27
ccaggagaaa gcatcagcac c                                             21

SEQ ID NO: 28               moltype = DNA   length = 20
FEATURE                     Location/Qualifiers
source                      1..20
                            mol_type = other DNA
                            organism = synthetic construct
SEQUENCE: 28
gcaatcagat acccagcccg                                               20

SEQ ID NO: 29               moltype = DNA   length = 24
FEATURE                     Location/Qualifiers
source                      1..24
                            mol_type = other DNA
                            organism = synthetic construct
SEQUENCE: 29
cggaatcaac gttgatgatt gcgg                                          24

SEQ ID NO: 30               moltype = DNA   length = 33
FEATURE                     Location/Qualifiers
source                      1..33
                            mol_type = other DNA
                            organism = synthetic construct
SEQUENCE: 30
aggcatattc gcacttcggc gtaaagatat ccg                                33

SEQ ID NO: 31               moltype = DNA   length = 34
FEATURE                     Location/Qualifiers
source                      1..34
                            mol_type = other DNA
                            organism = synthetic construct
SEQUENCE: 31
gccgaagtgc gaatatgcct gatggtgcaa cacc                               34

SEQ ID NO: 32               moltype = DNA   length = 22
```

```
FEATURE                 Location/Qualifiers
source                  1..22
                        mol_type = other DNA
                        organism = synthetic construct
SEQUENCE: 32
gatctgtctg acgtcaccct cg                                              22

SEQ ID NO: 33           moltype = DNA  length = 53
FEATURE                 Location/Qualifiers
source                  1..53
                        mol_type = other DNA
                        organism = synthetic construct
SEQUENCE: 33
ccacgggaca gtacgcacat gttttagagc tagaaatagc aagttaaaat aag            53

SEQ ID NO: 34           moltype = DNA  length = 51
FEATURE                 Location/Qualifiers
source                  1..51
                        mol_type = other DNA
                        organism = synthetic construct
SEQUENCE: 34
atgtgcgtac tgtcccgtgg actagtatta tacctaggac tgagctagct g              51

SEQ ID NO: 35           moltype = DNA  length = 24
FEATURE                 Location/Qualifiers
source                  1..24
                        mol_type = other DNA
                        organism = synthetic construct
SEQUENCE: 35
gtccagccag ttttagatgc ccag                                            24

SEQ ID NO: 36           moltype = DNA  length = 23
FEATURE                 Location/Qualifiers
source                  1..23
                        mol_type = other DNA
                        organism = synthetic construct
SEQUENCE: 36
gttacagtcg ccaattccat ccc                                             23

SEQ ID NO: 37           moltype = DNA  length = 28
FEATURE                 Location/Qualifiers
source                  1..28
                        mol_type = other DNA
                        organism = synthetic construct
SEQUENCE: 37
gaagaaataa ccggcgttca gcctgtgc                                        28

SEQ ID NO: 38           moltype = DNA  length = 41
FEATURE                 Location/Qualifiers
source                  1..41
                        mol_type = other DNA
                        organism = synthetic construct
SEQUENCE: 38
cgttctgata attcatgatc tttagctgtc ttggtttgcc c                         41

SEQ ID NO: 39           moltype = DNA  length = 30
FEATURE                 Location/Qualifiers
source                  1..30
                        mol_type = other DNA
                        organism = synthetic construct
SEQUENCE: 39
atgaattatc agaacgacga tttacgcatc                                      30

SEQ ID NO: 40           moltype = DNA  length = 44
FEATURE                 Location/Qualifiers
source                  1..44
                        mol_type = other DNA
                        organism = synthetic construct
SEQUENCE: 40
gtgaggacat ggtatatctc cttttacccg cgacgcgctt ttac                      44

SEQ ID NO: 41           moltype = DNA  length = 43
FEATURE                 Location/Qualifiers
source                  1..43
                        mol_type = other DNA
                        organism = synthetic construct
SEQUENCE: 41
gggtaaaagg agatatacca tgtcctcacg taaagagctt gcc                       43
```

```
SEQ ID NO: 42          moltype = DNA   length = 36
FEATURE                Location/Qualifiers
source                 1..36
                       mol_type = other DNA
                       organism = synthetic construct
SEQUENCE: 42
gtaggtgagt tacagcagtt cttttgcttt cgcaac                              36

SEQ ID NO: 43          moltype = DNA   length = 40
FEATURE                Location/Qualifiers
source                 1..40
                       mol_type = other DNA
                       organism = synthetic construct
SEQUENCE: 43
gcaaaagaac tgctgtaact cacctaccaa acaatgcccc                          40

SEQ ID NO: 44          moltype = DNA   length = 30
FEATURE                Location/Qualifiers
source                 1..30
                       mol_type = other DNA
                       organism = synthetic construct
SEQUENCE: 44
gcaaccattg gatcccaatg cttcgtttcg                                     30

SEQ ID NO: 45          moltype = DNA   length = 32
FEATURE                Location/Qualifiers
source                 1..32
                       mol_type = other DNA
                       organism = synthetic construct
SEQUENCE: 45
ggatccaatg gttgctgaat tgaccgcatt ac                                  32

SEQ ID NO: 46          moltype = DNA   length = 44
FEATURE                Location/Qualifiers
source                 1..44
                       mol_type = other DNA
                       organism = synthetic construct
SEQUENCE: 46
gttggacatg gtatatctcc ttttactggc gattgtcatt cgcc                     44

SEQ ID NO: 47          moltype = DNA   length = 43
FEATURE                Location/Qualifiers
source                 1..43
                       mol_type = other DNA
                       organism = synthetic construct
SEQUENCE: 47
gccagtaaaa ggagatatac catgtccaac aatggctcgt cac                      43

SEQ ID NO: 48          moltype = DNA   length = 42
FEATURE                Location/Qualifiers
source                 1..42
                       mol_type = other DNA
                       organism = synthetic construct
SEQUENCE: 48
ggctgaacgc cggttatttc ttcagttcag ccaggcttaa cc                       42

SEQ ID NO: 49          moltype = DNA   length = 44
FEATURE                Location/Qualifiers
source                 1..44
                       mol_type = other DNA
                       organism = synthetic construct
SEQUENCE: 49
ggtaaaagga gatataccat gactaaccct gtaatcggta ctcc                     44

SEQ ID NO: 50          moltype = DNA   length = 41
FEATURE                Location/Qualifiers
source                 1..41
                       mol_type = other DNA
                       organism = synthetic construct
SEQUENCE: 50
gtttggtagg tgagttattc attgtcacca gcagtagcag c                        41

SEQ ID NO: 51          moltype = DNA   length = 37
FEATURE                Location/Qualifiers
source                 1..37
                       mol_type = other DNA
                       organism = synthetic construct
SEQUENCE: 51
ggtgacaatg aataactcac ctaccaaaca atgcccc                             37
```

```
SEQ ID NO: 52           moltype = DNA  length = 54
FEATURE                 Location/Qualifiers
source                  1..54
                        mol_type = other DNA
                        organism = synthetic construct
SEQUENCE: 52
cagggttagt catggtatat ctccttttac ccgcgacgcg cttttactgc attc        54

SEQ ID NO: 53           moltype = DNA  length = 76
FEATURE                 Location/Qualifiers
source                  1..76
                        mol_type = other DNA
                        organism = synthetic construct
SEQUENCE: 53
ttgacagcta gctcagtcct aggtataata ctagtaaaga ggagaaaaag cttatgtcct  60
cacgtaaaga gcttgc                                                  76

SEQ ID NO: 54           moltype = DNA  length = 27
FEATURE                 Location/Qualifiers
source                  1..27
                        mol_type = other DNA
                        organism = synthetic construct
SEQUENCE: 54
ttacagcagt tcttttgctt tcgcaac                                      27

SEQ ID NO: 55           moltype = DNA  length = 25
FEATURE                 Location/Qualifiers
source                  1..25
                        mol_type = other DNA
                        organism = synthetic construct
SEQUENCE: 55
gtgatatcgc caataccgga ttacg                                        25

SEQ ID NO: 56           moltype = DNA  length = 40
FEATURE                 Location/Qualifiers
source                  1..40
                        mol_type = other DNA
                        organism = synthetic construct
SEQUENCE: 56
ggactgagct agctgtcaat gcggtgagtt caggttccgg                        40

SEQ ID NO: 57           moltype = DNA  length = 45
FEATURE                 Location/Qualifiers
source                  1..45
                        mol_type = other DNA
                        organism = synthetic construct
SEQUENCE: 57
gcaaaagaac tgctgtaaca ggcgttctac ataaaacgct tacgc                  45

SEQ ID NO: 58           moltype = DNA  length = 23
FEATURE                 Location/Qualifiers
source                  1..23
                        mol_type = other DNA
                        organism = synthetic construct
SEQUENCE: 58
ggcgatgtgt tgtgtgtaat tgg                                          23

SEQ ID NO: 59           moltype = DNA  length = 54
FEATURE                 Location/Qualifiers
source                  1..54
                        mol_type = other DNA
                        organism = synthetic construct
SEQUENCE: 59
ggcgaagaat atcatccatg gttttagagc tagaaatagc aagttaaaat aagg        54

SEQ ID NO: 60           moltype = DNA  length = 51
FEATURE                 Location/Qualifiers
source                  1..51
                        mol_type = other DNA
                        organism = synthetic construct
SEQUENCE: 60
catggatgat attcttcgcc actagtatta tacctaggac tgagctagct g           51

SEQ ID NO: 61           moltype = DNA  length = 21
FEATURE                 Location/Qualifiers
source                  1..21
                        mol_type = other DNA
                        organism = synthetic construct
```

-continued

```
SEQUENCE: 61
cgcattttga ctgggttcgg c                                             21

SEQ ID NO: 62          moltype = DNA  length = 22
FEATURE                Location/Qualifiers
source                 1..22
                       mol_type = other DNA
                       organism = synthetic construct
SEQUENCE: 62
gcggcactgt tcgtgataa cc                                             22

SEQ ID NO: 63          moltype = DNA  length = 75
FEATURE                Location/Qualifiers
source                 1..75
                       mol_type = other DNA
                       organism = synthetic construct
SEQUENCE: 63
ttgacagcta gctcagtcct aggtataata ctagtaaaga ggagaaaaag cttatgtcca   60
acaatggctc gtcac                                                   75

SEQ ID NO: 64          moltype = DNA  length = 39
FEATURE                Location/Qualifiers
source                 1..39
                       mol_type = other DNA
                       organism = synthetic construct
SEQUENCE: 64
gattgagagt tttatttctt cagttcagcc aggcttaac                          39

SEQ ID NO: 65          moltype = DNA  length = 25
FEATURE                Location/Qualifiers
source                 1..25
                       mol_type = other DNA
                       organism = synthetic construct
SEQUENCE: 65
gtatctcatc gagaacttgc ctgcc                                         25

SEQ ID NO: 66          moltype = DNA  length = 39
FEATURE                Location/Qualifiers
source                 1..39
                       mol_type = other DNA
                       organism = synthetic construct
SEQUENCE: 66
gactgagcta gctgtcaaac cgttccagag aggggggacc                         39

SEQ ID NO: 67          moltype = DNA  length = 35
FEATURE                Location/Qualifiers
source                 1..35
                       mol_type = other DNA
                       organism = synthetic construct
SEQUENCE: 67
gaagaaataa aactctcaat ctgatcggtt cctgc                              35

SEQ ID NO: 68          moltype = DNA  length = 21
FEATURE                Location/Qualifiers
source                 1..21
                       mol_type = other DNA
                       organism = synthetic construct
SEQUENCE: 68
gtgcggatta aatcccgcga c                                             21

SEQ ID NO: 69          moltype = DNA  length = 54
FEATURE                Location/Qualifiers
source                 1..54
                       mol_type = other DNA
                       organism = synthetic construct
SEQUENCE: 69
ggtgaaaacg actatcacgg gttttagagc tagaaatagc aagttaaaat aagg         54

SEQ ID NO: 70          moltype = DNA  length = 51
FEATURE                Location/Qualifiers
source                 1..51
                       mol_type = other DNA
                       organism = synthetic construct
SEQUENCE: 70
ccgtgatagt cgttttcacc actagtatta tacctaggac tgagctagct g            51

SEQ ID NO: 71          moltype = DNA  length = 23
FEATURE                Location/Qualifiers
source                 1..23
```

```
                          mol_type = other DNA
                          organism = synthetic construct
SEQUENCE: 71
cggatacaat gaccagttcc tgg                                             23

SEQ ID NO: 72             moltype = DNA   length = 19
FEATURE                   Location/Qualifiers
source                    1..19
                          mol_type = other DNA
                          organism = synthetic construct
SEQUENCE: 72
cggtttccag tgccacgtc                                                  19

SEQ ID NO: 73             moltype = DNA   length = 21
FEATURE                   Location/Qualifiers
source                    1..21
                          mol_type = other DNA
                          organism = synthetic construct
SEQUENCE: 73
ggcaacactt tgccgttgtg g                                               21

SEQ ID NO: 74             moltype = DNA   length = 32
FEATURE                   Location/Qualifiers
source                    1..32
                          mol_type = other DNA
                          organism = synthetic construct
SEQUENCE: 74
cataatcgcc gaactggcga aaacaaactg gc                                   32

SEQ ID NO: 75             moltype = DNA   length = 34
FEATURE                   Location/Qualifiers
source                    1..34
                          mol_type = other DNA
                          organism = synthetic construct
SEQUENCE: 75
tcgccagttc ggcgattatg cgagaaccaa atcc                                 34

SEQ ID NO: 76             moltype = DNA   length = 23
FEATURE                   Location/Qualifiers
source                    1..23
                          mol_type = other DNA
                          organism = synthetic construct
SEQUENCE: 76
cgatgagtgg cgtaactatc cgg                                             23

SEQ ID NO: 77             moltype = DNA   length = 54
FEATURE                   Location/Qualifiers
source                    1..54
                          mol_type = other DNA
                          organism = synthetic construct
SEQUENCE: 77
ggtgaaaata gcgtcatcgg gttttagagc tagaaatagc aagttaaaat aagg            54

SEQ ID NO: 78             moltype = DNA   length = 51
FEATURE                   Location/Qualifiers
source                    1..51
                          mol_type = other DNA
                          organism = synthetic construct
SEQUENCE: 78
ccgatgacgc tattttcacc actagtatta tacctaggac tgagctagct g              51

SEQ ID NO: 79             moltype = DNA   length = 21
FEATURE                   Location/Qualifiers
source                    1..21
                          mol_type = other DNA
                          organism = synthetic construct
SEQUENCE: 79
gtcaacatgc agcgccagat t                                               21

SEQ ID NO: 80             moltype = DNA   length = 21
FEATURE                   Location/Qualifiers
source                    1..21
                          mol_type = other DNA
                          organism = synthetic construct
SEQUENCE: 80
gatctacaac gtgcgtacgc c                                               21

SEQ ID NO: 81             moltype = DNA   length = 22
FEATURE                   Location/Qualifiers
```

```
source                   1..22
                         mol_type = other DNA
                         organism = synthetic construct
SEQUENCE: 81
cgtgagtatt tgcgtgagct gc                                              22

SEQ ID NO: 82            moltype = DNA   length = 30
FEATURE                  Location/Qualifiers
source                   1..30
                         mol_type = other DNA
                         organism = synthetic construct
SEQUENCE: 82
acgaggtttc tctctctacg ccctcacccg                                      30

SEQ ID NO: 83            moltype = DNA   length = 30
FEATURE                  Location/Qualifiers
source                   1..30
                         mol_type = other DNA
                         organism = synthetic construct
SEQUENCE: 83
cgtagagaga gaaacctcgt gcggtggttg                                      30

SEQ ID NO: 84            moltype = DNA   length = 27
FEATURE                  Location/Qualifiers
source                   1..27
                         mol_type = other DNA
                         organism = synthetic construct
SEQUENCE: 84
ggtcttacca atttcatgtc tgtgacg                                         27

SEQ ID NO: 85            moltype = DNA   length = 54
FEATURE                  Location/Qualifiers
source                   1..54
                         mol_type = other DNA
                         organism = synthetic construct
SEQUENCE: 85
aatcaccaca aagaatacgg gttttagagc tagaaatagc aagttaaaat aagg           54

SEQ ID NO: 86            moltype = DNA   length = 51
FEATURE                  Location/Qualifiers
source                   1..51
                         mol_type = other DNA
                         organism = synthetic construct
SEQUENCE: 86
cagctagctc agtcctaggt ataatactag taatcaccac aaagaatacg g              51

SEQ ID NO: 87            moltype = DNA   length = 20
FEATURE                  Location/Qualifiers
source                   1..20
                         mol_type = other DNA
                         organism = synthetic construct
SEQUENCE: 87
ttggcgcagg taaagttcgt                                                 20

SEQ ID NO: 88            moltype = DNA   length = 20
FEATURE                  Location/Qualifiers
source                   1..20
                         mol_type = other DNA
                         organism = synthetic construct
SEQUENCE: 88
tgttttgcca gttcgcgttc                                                 20

SEQ ID NO: 89            moltype = DNA   length = 25
FEATURE                  Location/Qualifiers
source                   1..25
                         mol_type = other DNA
                         organism = synthetic construct
SEQUENCE: 89
gcggcgaagg tctgtatttt atcga                                           25

SEQ ID NO: 90            moltype = DNA   length = 38
FEATURE                  Location/Qualifiers
source                   1..38
                         mol_type = other DNA
                         organism = synthetic construct
SEQUENCE: 90
ctatctgagc tttcttctgt cctgacgatc tttatgag                             38

SEQ ID NO: 91            moltype = DNA   length = 49
```

```
FEATURE                 Location/Qualifiers
source                  1..49
                        mol_type = other DNA
                        organism = synthetic construct
SEQUENCE: 91
cgtcaggaca gaagaaagct cagatagcct caaattcctt attgggtgc          49

SEQ ID NO: 92           moltype = DNA  length = 26
FEATURE                 Location/Qualifiers
source                  1..26
                        mol_type = other DNA
                        organism = synthetic construct
SEQUENCE: 92
ctggcttttc aacatatggc cgatac                                   26

SEQ ID NO: 93           moltype = DNA  length = 54
FEATURE                 Location/Qualifiers
source                  1..54
                        mol_type = other DNA
                        organism = synthetic construct
SEQUENCE: 93
agaaaatata tgccaccagg gttttagagc tagaaatagc aagttaaaat aagg    54

SEQ ID NO: 94           moltype = DNA  length = 51
FEATURE                 Location/Qualifiers
source                  1..51
                        mol_type = other DNA
                        organism = synthetic construct
SEQUENCE: 94
cagctagctc agtcctaggt ataatactag tagaaaatat atgccaccag g       51

SEQ ID NO: 95           moltype = DNA  length = 27
FEATURE                 Location/Qualifiers
source                  1..27
                        mol_type = other DNA
                        organism = synthetic construct
SEQUENCE: 95
gagcagcatg aagaagagaa actgttc                                  27

SEQ ID NO: 96           moltype = DNA  length = 23
FEATURE                 Location/Qualifiers
source                  1..23
                        mol_type = other DNA
                        organism = synthetic construct
SEQUENCE: 96
ggcgtcagag aaagagatga cgc                                      23

SEQ ID NO: 97           moltype = DNA  length = 40
FEATURE                 Location/Qualifiers
source                  1..40
                        mol_type = other DNA
                        organism = synthetic construct
SEQUENCE: 97
ggtaaaagga gatataccat gacacgacaa aaagcaacgc                    40

SEQ ID NO: 98           moltype = DNA  length = 35
FEATURE                 Location/Qualifiers
source                  1..35
                        mol_type = other DNA
                        organism = synthetic construct
SEQUENCE: 98
gtttggtagg tgagttaacc acgacgtgtc gccag                         35

SEQ ID NO: 99           moltype = DNA  length = 34
FEATURE                 Location/Qualifiers
source                  1..34
                        mol_type = other DNA
                        organism = synthetic construct
SEQUENCE: 99
cgtcgtggtt aactcaccta ccaaacaatg cccc                          34

SEQ ID NO: 100          moltype = DNA  length = 50
FEATURE                 Location/Qualifiers
source                  1..50
                        mol_type = other DNA
                        organism = synthetic construct
SEQUENCE: 100
cttttttgtcg tgtcatggta tatctccttt tacccgcgac gcgcttttac        50
```

-continued

```
SEQ ID NO: 101         moltype = DNA  length = 53
FEATURE                Location/Qualifiers
source                 1..53
                       mol_type = other DNA
                       organism = synthetic construct
SEQUENCE: 101
ttgacagcta gctcagtcct aggtataata ctagtaaaga ggagaaaaag ctt           53
```